(12) United States Patent
Dong et al.

(10) Patent No.: US 11,810,277 B2
(45) Date of Patent: Nov. 7, 2023

(54) IMAGE ACQUISITION METHOD, APPARATUS, AND TERMINAL

(71) Applicant: Huawei Technologies Co., Ltd., Shenzhen (CN)

(72) Inventors: Chen Dong, Shenzhen (CN); Xin Ding, Beijing (CN); Yongtao Jiang, Shenzhen (CN); Zhizhi Guo, Shenzhen (CN); Wenmei Gao, Beijing (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 17/261,356

(22) PCT Filed: Jul. 16, 2019

(86) PCT No.: PCT/CN2019/096135
§ 371 (c)(1),
(2) Date: Jan. 19, 2021

(87) PCT Pub. No.: WO2020/015629
PCT Pub. Date: Jan. 23, 2020

(65) Prior Publication Data
US 2021/0289128 A1 Sep. 16, 2021

(30) Foreign Application Priority Data
Jul. 20, 2018 (CN) .......................... 201810806467.3

(51) Int. Cl.
*G06T 5/50* (2006.01)
*H04N 23/611* (2023.01)
*H04N 23/56* (2023.01)
*H04N 23/67* (2023.01)
*H04N 23/74* (2023.01)
(Continued)

(52) U.S. Cl.
CPC .............. *G06T 5/50* (2013.01); *G06V 10/141* (2022.01); *G06V 10/17* (2022.01); *G06V 40/165* (2022.01); *G06V 40/166* (2022.01); *G06V 40/171* (2022.01); *G06V 40/172* (2022.01); *H04N 23/56* (2023.01); *H04N 23/611* (2023.01);
(Continued)

(58) Field of Classification Search
None
See application file for complete search history.

(56) References Cited

U.S. PATENT DOCUMENTS 10,311,316 B2 * 6/2019 Matthews ............ A61B 5/1171
10,818,007 B2 * 10/2020 Purwar ................. G06T 7/0012
(Continued)

FOREIGN PATENT DOCUMENTS

CN 103152476 A 6/2013
CN 203195655 U 9/2013
(Continued)

*Primary Examiner* — Shadan E Haghani
(74) *Attorney, Agent, or Firm* — Conley Rose, P.C.

(57) ABSTRACT

An image acquisition method includes acquiring a first image based on a first photographing parameter, where the first image includes a first to-be-detected item, acquiring a second image based on a second photographing parameter, where the second image includes a second to-be-detected item, and determining, based on the first image and the second image, a detection result corresponding to the first to-be-detected item and a detection result corresponding to the second to-be-detected item.

20 Claims, 8 Drawing Sheets

(51) Int. Cl.
  *H04N 23/80* (2023.01)
  *G06V 10/10* (2022.01)
  *G06V 10/141* (2022.01)
  *G06V 40/16* (2022.01)
(52) U.S. Cl.
  CPC ............ *H04N 23/67* (2023.01); *H04N 23/74* (2023.01); *H04N 23/80* (2023.01)

(56) References Cited

U.S. PATENT DOCUMENTS

| | | | |
|---|---|---|---|
| 2002/0094127 A1 * | 7/2002 | Mitchell | H04N 19/60 382/250 |
| 2003/0063801 A1 | 4/2003 | Rubinstenn et al. | |
| 2006/0007434 A1 * | 1/2006 | Furman | G01N 21/9501 356/237.2 |
| 2011/0116691 A1 | 5/2011 | Chung et al. | |
| 2015/0324686 A1 * | 11/2015 | Julian | G06N 3/08 706/25 |
| 2017/0052021 A1 | 2/2017 | Rhoades | |
| 2018/0376072 A1 * | 12/2018 | Kwon | G06V 40/171 |

FOREIGN PATENT DOCUMENTS

| | | | | |
|---|---|---|---|---|
| CN | 103685875 A | | 3/2014 | |
| CN | 104168425 A | | 11/2014 | |
| CN | 104586364 A | * | 5/2015 | ........... A61B 5/0077 |
| CN | 104586364 A | | 5/2015 | |
| CN | 104732214 A | | 6/2015 | |
| CN | 105100605 A | | 11/2015 | |
| CN | 105116669 A | | 12/2015 | |
| CN | 105578953 A | | 5/2016 | |
| CN | 105704395 A | | 6/2016 | |
| CN | 105979008 A | | 9/2016 | |
| CN | 103491305 B | | 11/2016 | |
| CN | 106231185 A | | 12/2016 | |
| CN | 106264463 A | | 1/2017 | |
| CN | 106385542 A | | 2/2017 | |
| CN | 107038428 A | | 8/2017 | |
| CN | 106331513 B | | 10/2017 | |
| CN | 104735362 B | | 11/2017 | |
| CN | 107862663 A | | 3/2018 | |
| CN | 107959997 A | | 4/2018 | |
| CN | 108200351 A | | 6/2018 | |
| CN | 109219389 A | | 1/2019 | |
| EP | 2835748 A1 | * | 2/2015 | ....... G06F 16/24573 |
| JP | 2008182360 A | | 8/2008 | |
| JP | 2016112024 A | | 6/2016 | |
| WO | 2012166044 A1 | | 12/2012 | |
| WO | 2015120673 A1 | | 8/2015 | |
| WO | 2017161523 A1 | | 9/2017 | |

* cited by examiner

IMAGE ACQUISITION METHOD, APPARATUS, AND TERMINAL

CROSS-REFERENCE TO RELATED APPLICATIONS

This application is a U.S. National Stage of International Patent Application No. PCT/CN2019/096135 filed on Jul. 16, 2019, which claims priority to Chinese Patent Application No. 201810806467.3 filed on Jul. 20, 2018, both of which are hereby incorporated by reference in their entireties.

TECHNICAL FIELD

Embodiments of the present invention relate to the field of multimedia technologies, and in particular, to a multi-parameter image acquisition method, apparatus, and terminal.

BACKGROUND

People all like beauty. With the steady improvement of living standards, people are in hotter pursuit of beauty. People who pursue and advocate beauty pay much attention to skin health. Skin health detection refers to overall evaluation of skin conditions, including detection and evaluation on a plurality of detection items such as a skin type, a skin tone, a wrinkle, a fine line, a speckle, redness, acne, a pore, an under-eye dark circle, and under-eye puffiness. Based on these detection results, people can take pertinent skin care measures to keep skin healthy and beautiful.

Currently, in a conventional skin health detection method, a terminal first takes a photo of a particular body part of a user in a flash on state, and then determines a skin condition corresponding to the body part by detecting the photo, to obtain a corresponding skin care suggestion. It can be learned from above that, in the method, only the flash photo of the specific skin part is detected, and a definition of a detail feature of skin of the user usually cannot meet a detection precision requirement. In addition, an error may occur on a detection result due to impact of different ambient light and a focal length that are used when the flash photo is acquired. Consequently, the suggestion obtained by the user is inaccurate.

SUMMARY

Embodiments of the present invention provide an image acquisition method, apparatus, and terminal, to resolve a problem that a definition cannot meet a detection precision requirement because to-be-detected images corresponding to a plurality of to-be-detected items cannot be accurately obtained and one flash photo is used to detect different detection items.

According to a first aspect, an embodiment of the present invention provides an image acquisition method, which may specifically include: acquiring, by a terminal, at least one first image based on a first photographing parameter, where the first image includes a first to-be-detected item; and acquiring, by the terminal, at least one second image based on a second photographing parameter, where the second image includes a second to-be-detected item; the first photographing parameter includes a first light intensity and a first focal length, and the second photographing parameter includes a second light intensity and a second focal length; and the terminal includes a light emitting diode LED light source, the LED light source emits light in a first mode to provide the first light intensity, and the LED light source emits light in a second mode to provide the second light intensity.

In this solution, a plurality of photos (the first image and the second image) are acquired by using different photographing parameters (the first photographing parameter and the second photographing parameter), so that it can be ensured that blur degrees of depth of field positions and detail parts in to-be-detected images obtained in different photographing modes all meet detection precision, to ensure accuracy of subsequent detection results. It should be noted that, because different focal lengths (the first focal length and the second focal length) and different light intensities (the first light intensity and the second light intensity) are used, object blur degrees of different depth of field positions and object detail clarity degrees in the first image and the second image are different. The different focal lengths correspond to the object blur degrees of the different depths of field positions, and the different light intensities correspond to the object detail clarity degrees. In addition, all photographing processes of the method are subject to fully automatic continuous photographing, so that a user does not need to manually adjust a focal length and a light intensity, thereby improving user experience.

In an optional implementation, the "first mode" may include at least one of a flashlight mode, a preset light emitting mode, or a flash mode, an operating current of the LED light source in the flashlight mode is a first current, and an operating current of the LED light source in the preset light emitting mode is a second current.

In another optional implementation, the "second mode" may include at least one of the flashlight mode, the preset light emitting mode, or the flash mode.

In still another optional implementation, light intensities and lighting times of the LED light source in the "flashlight mode" and the "preset light emitting mode" are adjustable.

In yet another optional implementation, the "first to-be-detected item" and the "second to-be-detected item" may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis.

In yet another optional implementation, the "first to-be-detected item" may be classified into a first feature and a second feature based on a skin characteristic. The first feature includes at least one of the following: the skin tone, the speckle, or the redness. The second feature includes at least one of the following: the acne, the oil content, the wrinkle, the eye feature, the blackhead, the water content, the melanin, the porphyrin, or the pore. The "second to-be-detected item" may be classified into a third feature and a fourth feature based on a skin characteristic. The third feature includes at least one of the following: the blackhead, the eye feature, the melanin, the porphyrin, or the pore. The fourth feature includes at least one of the following: the skin tone, the speckle, the redness, the acne, the oil content, the wrinkle, or the water content.

The eye feature includes at least one of the following: the under-eye puffiness, the under-eye dark circle, or the under-eye fine line. The wrinkle includes at least one of the following: the nasolabial fold, the forehead wrinkle, the mountain root wrinkle, the upper lip wrinkle, or the downward wrinkle at the corner of the mouth. The water content includes at least one of the following: the water content of epidermis or the water content of dermis.

In yet another optional implementation, the method may further include: detecting, by the terminal, the first image and the second image, to determine detection results of the first to-be-detected item and the second to-be-detected item.

In yet another optional implementation, the step of "detecting, by the terminal, the first image and the second image, to determine detection results of the first to-be-detected item and the second to-be-detected item" may specifically include: detecting, by the terminal, the first image and the second image, to separately determine the detection results of the first to-be-detected item and the second to-be-detected item, where the first image includes the first to-be-detected item, and the second image includes the second detection item.

In yet another optional implementation, the step of "determining, by the terminal, detection results of the first to-be-detected item and the second to-be-detected item based on a to-be-detected image" may specifically include: when there are a plurality of to-be-detected images, synthesizing, by the terminal, the to-be-detected images into one detection image; and determining, by the terminal, the detection results of the first to-be-detected item and the second to-be-detected item based on the synthesized to-be-detected image.

In yet another optional implementation, the step of "determining, by the terminal, detection results of the first to-be-detected item and the second to-be-detected item based on a to-be-detected image" may specifically include: when there are a plurality of to-be-detected images, detecting, by the terminal, each of the plurality of to-be-detected images, to determine detection results corresponding to the first to-be-detected item and the second to-be-detected item in each to-be-detected image; and synthesizing, by the terminal, detection results of all the images, to determine the detection results of the first to-be-detected item and the second to-be-detected item.

In yet another optional implementation, the step of "detecting, by the terminal, the first image and the second image, to determine detection results of the first to-be-detected item and the second to-be-detected item" may specifically include: when at least one of the first to-be-detected item in the first image or the second to-be-detected item in the second image is in a blurred state, deleting, by the terminal, at least one of the first image or the second image; re-determining, by the terminal, at least one of the first photographing parameter or the second photographing parameter, to acquire at least one of the first image or the second image; and determining, by the terminal, a detection result of the at least one of the first to-be-detected item or the second to-be-detected item based on the at least one of the re-acquired first image or the re-acquired second image.

In yet another optional implementation, before the step of "detecting, by the terminal, the first image and the second image, to determine detection results of the first to-be-detected item and the second to-be-detected item", the method may further include: determining, by the terminal, to enter a to-be-detected item modeling mode, where the to-be-detected item modeling mode includes modeling models for detecting the first to-be-detected item and the second to-be-detected item.

In yet another optional implementation, the step of "detecting, by the terminal, the first image and the second image, to determine detection results of the first to-be-detected item and the second to-be-detected item" may specifically include: detecting, by the terminal, the first image and the second image based on the modeling models of the first to-be-detected item and the second to-be-detected item, to determine the detection results of the first to-be-detected item and the second to-be-detected item.

In yet another optional implementation, before the step of "determining, by the terminal, to enter a to-be-detected item modeling mode", the method may further include: determining, by the terminal, whether the modeling models in the to-be-detected item modeling mode are invalid modeling models.

In yet another optional implementation, the step of "determining, by the terminal, whether the modeling models in the to-be-detected item modeling mode are invalid modeling models" may specifically include: when time intervals between a first moment and moments at which the modeling models are established are greater than a threshold, determining that the modeling models are invalid modeling models, where the first moment is a moment at which the terminal invokes the modeling models.

In yet another optional implementation, the step of "acquiring, by a terminal, at least one first image based on a first photographing parameter, and acquiring, by the terminal, at least two second images based on a second photographing parameter" may specifically include: when the models are invalid modeling models, photographing, by the terminal, a first image and a first modeling image based on the first photographing parameter, where the first modeling image is used to establish a modeling model for the first to-be-detected image; and photographing, by the terminal, a second image and a second modeling image based on the second photographing parameter, where the second modeling image is used to establish a modeling model for the second to-be-detected image.

In yet another optional implementation, the step of "acquiring, by a terminal, at least one first image based on a first photographing parameter, and acquiring, by the terminal, at least two second images based on a second photographing parameter" may specifically include: when the terminal meets a photographing condition, acquiring, by the terminal, at least one first image based on the first photographing parameter, and acquiring, by the terminal, at least two second images based on the second photographing parameter, where the photographing condition includes an ambient light intensity and determining, by the terminal, that the first to-be-detected item and the second to-be-detected item are within a photographing range.

In yet another optional implementation, a manner of determining the "first focal length" and the "second focal length" includes at least one of point focusing, area focusing, or full-face focusing.

According to a second aspect, an embodiment of the present invention provides an image acquisition terminal. The terminal may include: one or more processors, a memory, a plurality of application programs, and a light emitting diode LED; and one or more computer programs, where the one or more computer programs are stored in the memory, the one or more computer programs include an instruction, and when the instruction is executed by the terminal, the terminal is enabled to perform the following steps: acquiring at least one first image based on a first photographing parameter, where the first image includes a first to-be-detected item; and acquiring at least one second image based on a second photographing parameter, where the second image includes a second to-be-detected item; the first photographing parameter includes a first light intensity and a first focal length, and the second photographing parameter includes a second light intensity and a second focal length; and the LED provides an LED light source, the LED light source emits light in a first mode to provide the first light intensity, and the LED light source emits light in a second mode to provide the second light intensity.

In this solution, the terminal acquires a plurality of photos (the first image and the second image) by using different photographing parameters (the first photographing parameter and the second photographing parameter), so that it can be ensured that blur degrees of depth of field positions and detail parts in to-be-detected images obtained in different photographing modes all meet detection precision, to ensure accuracy of subsequent detection results. It should be noted that, because different focal lengths (the first focal length and the second focal length) and different light intensities (the first light intensity and the second light intensity) are used, object blur degrees of different depth of field positions and object detail clarity degrees in the first image and the second image are different. The different focal lengths correspond to the object blur degrees of the different depths of field positions, and the different light intensities correspond to the different object detail clarity degrees. In addition, all photographing processes of the method are subject to fully automatic continuous photographing, so that a user does not need to manually adjust a focal length and a light intensity, thereby improving user experience.

In an optional implementation, the "first mode" may include at least one of a flashlight mode, a preset light emitting mode, or a flash mode, an operating current of the LED light source in the flashlight mode is a first current, and an operating current of the LED light source in the preset light emitting mode is a second current.

In another optional implementation, the "second mode" may include at least one of the flashlight mode, the preset light emitting mode, or the flash mode.

In still another optional implementation, light intensities and lighting times in the "flashlight mode" and the "preset light emitting mode" are adjustable.

In yet another optional implementation, the "first to-be-detected item" and the "second to-be-detected item" may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis.

In yet another optional implementation, the "first to-be-detected item" may be classified into a first feature and a second feature based on a skin characteristic. The first feature includes at least one of the following: the skin tone, the speckle, or the redness. The second feature includes at least one of the following: the acne, the oil content, the wrinkle, the eye feature, the blackhead, the water content, the melanin, the porphyrin, or the pore. The "second to-be-detected item" may be classified into a third feature and a fourth feature based on a skin characteristic. The third feature includes at least one of the following: the blackhead, the eye feature, the melanin, the porphyrin, or the pore. The fourth feature includes at least one of the following: the skin tone, the speckle, the redness, the acne, the oil content, the wrinkle, or the water content.

The eye feature includes at least one of the following: the under-eye puffiness, the under-eye dark circle, or the under-eye fine line. The wrinkle includes at least one of the following: the nasolabial fold, the forehead wrinkle, the mountain root wrinkle, the upper lip wrinkle, or the downward wrinkle at the corner of the mouth. The water content includes at least one of the following: the water content of epidermis or the water content of dermis.

In yet another optional implementation, the terminal may further perform the following step: detecting the first image and the second image, to determine detection results of the first to-be-detected item and the second to-be-detected item.

In yet another optional implementation, the terminal may specifically perform the following step: detecting the first image and the second image, to separately determine the detection results of the first to-be-detected item and the second to-be-detected item, where the first image includes the first to-be-detected item, and the second image includes the second detection item. In yet another optional implementation, the terminal may specifically perform the following step: when there are a plurality of to-be-detected images, synthesizing the to-be-detected images into one detection image, and determining the detection results of the first to-be-detected item and the second to-be-detected item based on the synthesized to-be-detected image.

In yet another optional implementation, the terminal may specifically perform the following step: when there are a plurality of to-be-detected images, detecting each of the plurality of to-be-detected images, to determine detection results corresponding to the first to-be-detected item and the second to-be-detected item in each to-be-detected image; and synthesizing detection results of all the images, to determine the detection results of the first to-be-detected item and the second to-be-detected item.

In yet another optional implementation, the terminal may specifically perform the following step: when at least one of the first to-be-detected item in the first image or the second to-be-detected item in the second image is in a blurred state, deleting at least one of the first image or the second image; re-determining at least one of the first photographing parameter or the second photographing parameter, to acquire at least one of the first image or the second image; and determining a detection result of the at least one of the first to-be-detected item or the second to-be-detected item based on the at least one of the re-acquired first image or the re-acquired second image.

In yet another optional implementation, the terminal may further perform the following step: determining to enter a to-be-detected item modeling mode, where the to-be-detected item modeling mode includes modeling models for detecting the first to-be-detected item and the second to-be-detected item.

In yet another optional implementation, the terminal may specifically perform the following step: detecting the first image and the second image based on the modeling models of the first to-be-detected item and the second to-be-detected item, to determine the detection results of the first to-be-detected item and the second to-be-detected item.

In yet another optional implementation, the terminal may further perform the following step: determining whether the modeling models in the to-be-detected item modeling mode are invalid modeling models.

In yet another optional implementation, the terminal may specifically perform the following step: when time intervals between a first moment and moments at which the modeling models are established are greater than a threshold, determining that the modeling models are invalid modeling models, where the first moment is a moment at which the terminal invokes the modeling models.

In yet another optional implementation, the terminal may specifically perform the following step: when the models are invalid modeling models, photographing a first image and a first modeling image based on the first photographing parameter, where the first modeling image is used to establish a modeling model for the first to-be-detected image; and photographing a second image and a second modeling image based on the second photographing parameter, where the second modeling image is used to establish a modeling model for the second to-be-detected image.

In yet another optional implementation, the terminal may specifically perform the following step: when the terminal meets a photographing condition, acquiring at least one first image based on the first photographing parameter, and acquiring at least two second images based on the second photographing parameter, where the photographing condition includes an ambient light intensity and determining that the first to-be-detected item and the second to-be-detected item are within a photographing range.

In yet another optional implementation, a manner of determining the "first focal length" and the "second focal length" includes at least one of point focusing, area focusing, or full-face focusing.

According to a third aspect, an embodiment of the present invention provides an image acquisition apparatus. The apparatus may include: a processing module, which may be configured to acquire at least one first image based on a first photographing parameter, where the first image includes a first to-be-detected item; and acquire at least one second image based on a second photographing parameter, where the second image includes a second to-be-detected item; and the first photographing parameter includes a first light intensity and a first focal length, and the second photographing parameter includes a second light intensity and a second focal length; and a lighting module, where the lighting module may include a light emitting diode LED light source, the LED light source is configured to emit light in a first mode to provide the first light intensity, and the LED light source emits light in a second mode to provide the second light intensity.

In this solution, the apparatus acquires a plurality of photos (the first image and the second image) by using different photographing parameters (the first photographing parameter and the second photographing parameter), so that it can be ensured that blur degrees of depth of field positions and detail parts in to-be-detected images obtained in different photographing modes all meet detection precision, to ensure accuracy of subsequent detection results. It should be noted that, because different focal lengths (the first focal length and the second focal length) and different light intensities (the first light intensity and the second light intensity) are used, object blur degrees of different depth of field positions and object detail clarity degrees in the first image and the second image are different. The different focal lengths correspond to the object blur degrees of the different depths of field positions, and the different light intensities correspond to the different object detail clarity degrees. In addition, all photographing processes of the method are subject to fully automatic continuous photographing, so that a user does not need to manually adjust a focal length and a light intensity, thereby improving user experience.

In an optional implementation, the "first mode" may include at least one of a flashlight mode, a preset light emitting mode, or a flash mode, an operating current of the LED light source in the flashlight mode is a first current, and an operating current of the LED light source in the preset light emitting mode is a second current.

In another optional implementation, the "second mode" may include at least one of the flashlight mode, the preset light emitting mode, or the flash mode.

In still another optional implementation, light intensities and lighting times in the "flashlight mode" and the "preset light emitting mode" are adjustable.

In yet another optional implementation, the "first to-be-detected item" and the "second to-be-detected item" may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis.

In yet another optional implementation, the "first to-be-detected item" may be classified into a first feature and a second feature based on a skin characteristic. The first feature includes at least one of the following: the skin tone, the speckle, or the redness. The second feature includes at least one of the following: the acne, the oil content, the wrinkle, the eye feature, the blackhead, the water content, the melanin, the porphyrin, or the pore. The "second to-be-detected item" may be classified into a third feature and a fourth feature based on a skin characteristic. The third feature includes at least one of the following: the blackhead, the eye feature, the melanin, the porphyrin, or the pore. The fourth feature includes at least one of the following: the skin tone, the speckle, the redness, the acne, the oil content, the wrinkle, or the water content.

The eye feature includes at least one of the following: the under-eye puffiness, the under-eye dark circle, or the under-eye fine line. The wrinkle includes at least one of the following: the nasolabial fold, the forehead wrinkle, the mountain root wrinkle, the upper lip wrinkle, or the downward wrinkle at the corner of the mouth. The water content includes at least one of the following: the water content of epidermis or the water content of dermis.

In yet another optional implementation, the apparatus may further include a detection module, which may be configured to detect the first image and the second image, to determine detection results of the first to-be-detected item and the second to-be-detected item.

In yet another optional implementation, the "detection module" may be specifically configured to detect the first image and the second image, to separately determine the detection results of the first to-be-detected item and the second to-be-detected item, where the first image includes the first to-be-detected item, and the second image includes the second detection item. In yet another optional implementation, the "detection module" may be specifically configured to: when there are a plurality of to-be-detected images, synthesize the to-be-detected images into one detection image, and determine the detection results of the first to-be-detected item and the second to-be-detected item based on the synthesized to-be-detected image.

In yet another optional implementation, the "detection module" may be specifically configured to: when there are a plurality of to-be-detected images, detect each of the plurality of to-be-detected images, to determine detection results corresponding to the first to-be-detected item and the second to-be-detected item in each to-be-detected image;

and synthesize detection results of all the images, to determine the detection results of the first to-be-detected item and the second to-be-detected item.

In yet another optional implementation, the "detection module" may be specifically configured to: when at least one of the first to-be-detected item in the first image or the second to-be-detected item in the second image is in a blurred state, delete at least one of the first image or the second image; re-determine at least one of the first photographing parameter or the second photographing parameter, to acquire at least one of the first image or the second image; and determine a detection result of the at least one of the first to-be-detected item or the second to-be-detected item based on the at least one of the re-acquired first image or the re-acquired second image.

In yet another optional implementation, the apparatus may further include a modeling module, which may be configured to determine to enter a to-be-detected item modeling mode, where the to-be-detected item modeling mode includes modeling models for detecting the first to-be-detected item and the second to-be-detected item.

In yet another optional implementation, the "modeling module" may be specifically configured to: detect the first image and the second image based on the modeling models of the first to-be-detected item and the second to-be-detected item, to determine the detection results of the first to-be-detected item and the second to-be-detected item.

In yet another optional implementation, the apparatus may further include a determining module, which may be configured to determine whether the modeling models in the to-be-detected item modeling mode are invalid modeling models.

In yet another optional implementation, the "determining module" may be specifically configured to: when time intervals between a first moment and moments at which the modeling models are established are greater than a threshold, determine that the modeling models are invalid modeling models, where the first moment is a moment at which the apparatus invokes the modeling model.

In yet another optional implementation, the "modeling module" may be specifically configured to: when the models are invalid modeling models, photograph a first image and a first modeling image based on the first photographing parameter, where the first modeling image is used to establish a modeling model for the first to-be-detected image; and photograph a second image and a second modeling image based on the second photographing parameter, where the second modeling image is used to establish a modeling model for the second to-be-detected image.

In yet another optional implementation, the "processing module" may be specifically configured to: when the apparatus meets a photographing condition, acquire at least one first image based on the first photographing parameter, and acquire at least two second images based on the second photographing parameter, where the photographing condition includes an ambient light intensity and determining, by the apparatus, that the first to-be-detected item and the second to-be-detected item are within a photographing range.

In yet another optional implementation, a manner of determining the "first focal length" and the "second focal length" includes at least one of point focusing, area focusing, or full-face focusing.

According to a fourth aspect, an embodiment of the present invention provides a computer readable storage medium, including an instruction. When the instruction is run on a computer, the computer is enabled to perform the method according to any one of the first aspect or the possible implementations of the first aspect.

According to a fifth aspect, an embodiment of the present invention provides a computer program product including an instruction. When the instruction is run on a computer, the computer is enabled to perform the method according to any one of the first aspect or the possible implementations of the first aspect.

BRIEF DESCRIPTION OF DRAWINGS

FIG. 1$b$ is a schematic diagram of another application scenario of acquiring a face image by using a plurality of parameters according to an embodiment of the present invention;

DESCRIPTION OF EMBODIMENTS

For better understanding of the embodiments of the present invention, the following uses specific embodiments to provide further explanations with reference to the accompanying drawings, and the embodiments constitute no limitation to the embodiments of the present invention.

The embodiments of the present invention provide an image acquisition method, apparatus, and terminal, to acquire a plurality of photos (a first image and a second image) by using different photographing parameters (a first photographing parameter and a second photographing parameter), so that it can be ensured that blur degrees of depth of field positions and detail parts in to-be-detected images obtained in different photographing modes all meet detection precision, to ensure accuracy of subsequent detection results. It should be noted that, because different focal lengths (a first focal length and a second focal length) and different light intensities (a first light intensity and a second light intensity) are used, object blur degrees of different depth of field positions and object detail clarity degrees in the first image and the second image are different. The different focal lengths correspond to the object blur degrees of the different depths of field positions, and the different light intensities correspond to the different object detail clarity degrees. In addition, all photographing processes of the method are subject to fully automatic continuous photographing, so that a user does not need to manually adjust a focal length and a light intensity, thereby improving user experience. The terminal may adjust the first light intensity and the second light intensity by changing a voltage or a current of a light emitting diode. The first to-be-detected item and the second to-be-detected item above may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis. A manner of adjusting the first focal length and the second focal length includes at least one of point focusing, area focusing, or full-face focusing.

Figure 1A:
FIG. 1$a$ is a schematic diagram of an application scenario of acquiring a face image by using a plurality of parameters according to an embodiment of the present invention.
Figure 1B:
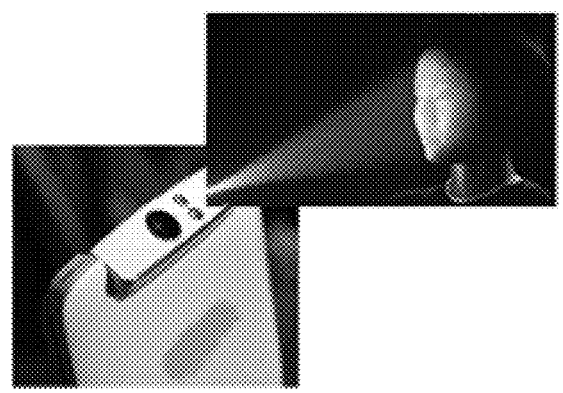

FIG. 1a is a schematic diagram of an application scenario of acquiring a face image by using a plurality of parameters according to an embodiment of the present invention. As shown in FIG. 1a, the application scenario may include: A user adjusts a position of a terminal (or a camera), so that the terminal (or the camera) meets a photographing condition. The photographing condition may include an ambient light intensity and determining that to-be-detected items (a first to-be-detected item and a second to-be-detected item) are within a photographing range (for example, the user adjusts the position of the camera or the terminal, so that facial skin of the user is within the photographing range of the camera). Alternatively, as shown in FIG. 1b, when a camera of a terminal is a rotatable camera, the terminal automatically adjusts a position of the camera based on to-be-detected items, so that the terminal meets a photographing condition (for example, the terminal adjusts the position of the camera based on an acquired picture, so that all facial skin of a user is within a photographing range of the camera).

The terminal above may include a mobile phone, a tablet computer, a notebook computer, and the like. The terminal may include at least the camera, a processor, a memory, an LED light source, and a display screen. The camera may be configured to acquire a first image and a second image, and may further adjust a focal length based on different photographing parameters. The LED light source may provide light for at least one of a flash mode, a flashlight mode, or a preset light emitting mode in a first mode or a second mode. It should be noted that, light emitting times of the LED light source in the flash mode, the flashlight mode, and the preset light emitting mode are different. For example, a light emitting time of the LED light source in the flash mode is the shortest, light emitting times of the LED light source in the flashlight mode and the preset light emitting mode may be the same or may be different, and the light emitting times of the LED light source in the flashlight mode and the preset light emitting mode are adjustable. Generally, a light emitting time in the flashlight mode is longer than a light emitting time in the preset light emitting mode. The LED light source may be a built-in flash of the mobile phone, or an external strobe connected to the mobile phone through a particular interface. The built-in flash of the mobile phone may be a dual-color-temperature flash. In the preset light emitting mode, a light intensity may be provided by at least one LED light source of the dual-color-temperature flash, and a light intensity of at least one LED light source of the dual-color-temperature flash is adjustable. Optionally, the light intensity is adjusted by changing an operating current of the LED light source. For example, an operating current of the LED light source in the flashlight mode is 180 milliamperes, and an operating current of the LED light source in the preset light emitting mode is 120 milliamperes. Light intensities in the flashlight mode may be divided into 0 to N levels, and each level has a different light intensity. The preset light emitting mode may include two time periods. In a first time period, an operating current of the LED light source is 60 milliamperes. In a second time period, an operating current of the LED light source is 100 milliamperes.

The memory may be configured to store a software program. The processor performs functions of the terminal by running the software program stored in the memory (for example, the processor invokes the memory, the camera, and the flash to acquire the first image and the second image and determine definitions of the to-be-detected items). The processor may be further configured to detect the first image and the second image, to determine a detection result of the first to-be-detected item in the first image and a detection result of the second to-be-detected item in the second image. The display screen may be configured to display at least one of the following: the first image and the second image, a synthesized image of the first image and the second image, the detection result of the first to-be-detected item in the first image, or the detection result of the second to-be-detected item in the second image.

For ease of description, in the present invention, the following uses a mobile phone as an example for specific description of a terminal.

Figure 2:
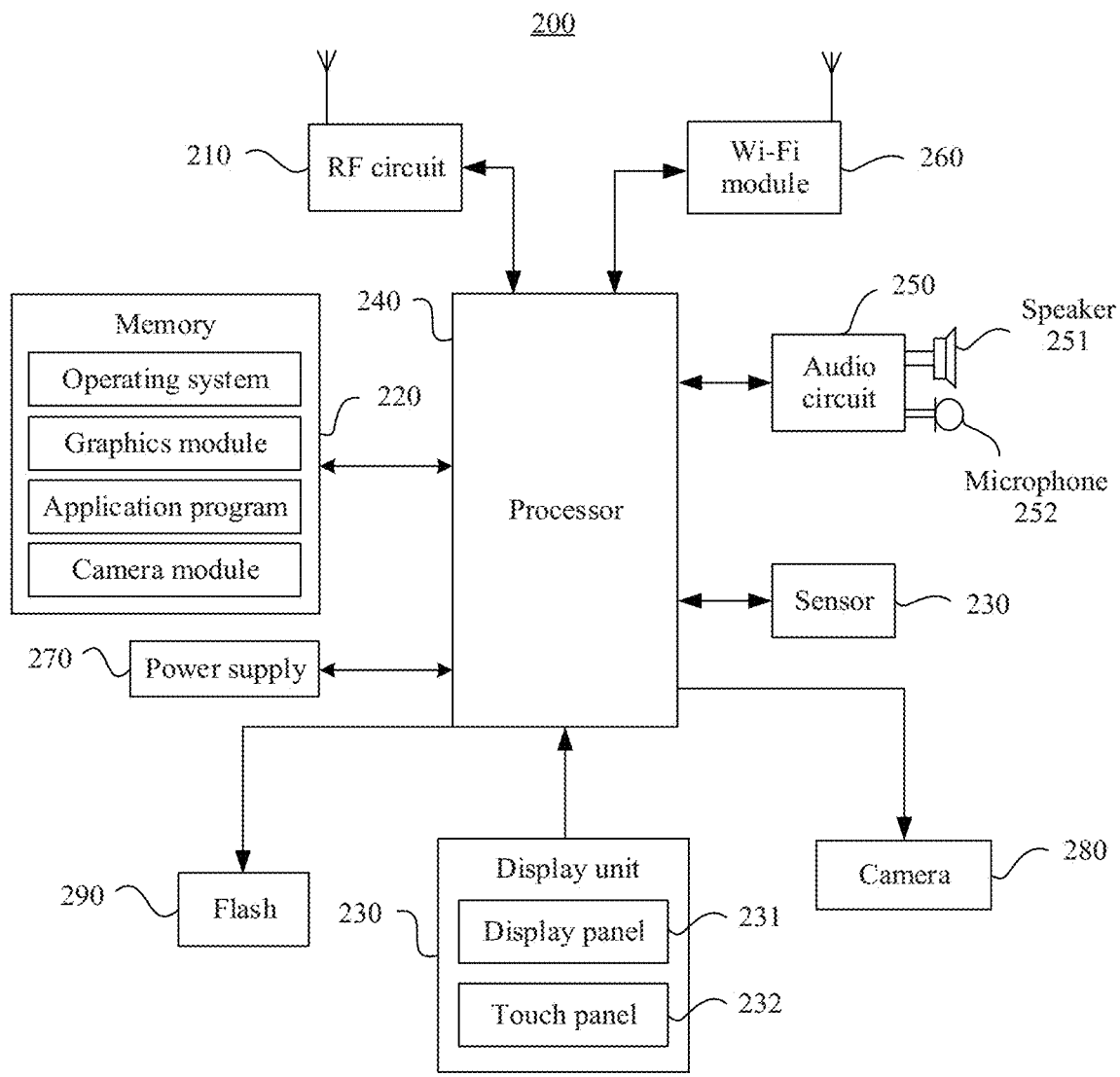
FIG. 2 is a schematic structural diagram of a terminal according to an embodiment of the present invention.

FIG. 2 is a schematic structural diagram of a terminal according to an embodiment of the present invention. FIG. 2 is a schematic structural diagram of a mobile phone related to an embodiment of the present invention. FIG. 2 is a block diagram of a partial structure of a mobile phone 200. The mobile phone 200 includes: a radio frequency (radio frequency, RF) circuit 210, a memory 220, a display unit 230, a sensor 230, a processor 240, an audio circuit 250, a wireless fidelity (wireless fidelity, Wi-Fi) module 260, a power supply 270, a camera 280, and a flash 290. A person skilled in the art may understand that the structure of the mobile phone shown in FIG. 2 does not constitute a limitation on the mobile phone, and the mobile phone may include more or fewer components than those shown in the figure, or have some components combined, or have a different component arrangement.

The following describes the components of the mobile phone 200 in detail with reference to FIG. 2.

The RF circuit 210 may be configured to receive and send signals during information receiving and sending processes or during a call. The RF circuit 210 receives downlink information of a base station, and sends the downlink information of the base station to the processor 240. Generally, the RF circuit includes, but is not limited to, an antenna, at least one amplifier, a transceiver, a coupler, a low noise amplifier (low noise amplifier, LNA), a duplexer, and the like. In addition, the RF circuit 210 may further communicate with at least one of a network or another device through wireless communication. The wireless communication may use any communications standard or protocol, including but not limited to, a global system for mobile communications (global system of mobile communication, GSM), a general packet radio service (general packet radio service, GPRS), code division multiple access (code division multiple access, CDMA), wideband code division multiple access (wideband code division multiple access, WCDMA), long term evolution (long term evolution, LTE), an email, and a short message service (short messaging service, SMS), and the like.

The memory 220 may be configured to store a software program and a module, and may mainly include a program storage area and a data storage area. The program storage area may store an operating system, an application program required by at least one function (for example, a sound playback function or an image playback function), and the like. The data storage area may store data (for example, a modeling image required in modeling) created depending on use of the mobile phone 200, and the like. The memory 220 may further include a high-speed random access memory, and may further include a non-volatile memory, for example, at least one magnetic disk storage device, a flash memory device, or another volatile solid-state storage device. In addition, a touch/motion module included in the memory 220 is configured to detect touch between an object or a finger and a touchscreen or a click wheel, capture a speed (a direction and magnitude) and an acceleration (a change of the magnitude or the direction) of the touch, and determine a type of a touch event.

The display unit 230 may be configured to display information entered by the user or information provided for the user, and menus of the mobile phone 100. The display unit 230 may include a display panel 231 and a touch panel 232. The display panel 231 may be configured in a form of a liquid crystal display (liquid crystal display, LCD), an organic light emitting diode (organic light emitting diode, OLED), or the like. Further, the touch panel 232 may cover the display panel 231. After detecting a touch operation on or near the touch panel 232, the touch panel 232 transmits the touch operation to the processor 240 to determine a type of a touch event. Subsequently, the processor 240 provides a corresponding visual output on the display panel 231 based on the type of the touch event. In FIG. 2, the touch panel 232 and the display panel 231 implement input and output functions of the mobile phone 200 as two separate components. However, in some embodiments, the touch panel 232 and the display panel 231 may be integrated to implement the input and output functions of the mobile phone 100. In addition, for the present invention, the display unit 230 (for example, a display) may further display at least one of the following: a first image and a second image, a synthesized image of the first image and the second image, a detection result of a first to-be-detected item in the first image, or a detection result of a second to-be-detected item in the second image.

The mobile phone 200 may further include at least one sensor 230, for example, an optical sensor, a motion sensor, and another sensor. Specifically, the optical sensor may include an ambient light sensor and a proximity sensor. The ambient light sensor may adjust luminance of the display panel 231 based on brightness of ambient light. The proximity sensor may turn off the display panel 231 and/or backlight when the mobile phone 200 is moved to an ear. As a type of motion sensor, an accelerometer sensor may detect magnitude of accelerations in different directions (generally on three axes), may detect magnitude and a direction of gravity when being stationary, and may be applied to mobile phone posture recognition applications (for example, switching between landscape orientation and portrait orientation, a related game, and magnetometer posture calibration), a function related to vibration recognition (for example, a pedometer or a knock), and the like. Other sensors such as a gyroscope, a barometer, a hygrometer, a thermometer, and an infrared sensor that may be configured in the mobile phone 200 are not described herein.

The audio circuit 250, a speaker 251, and a microphone 252 may provide an audio interface between the user and the mobile phone 200. The audio circuit 250 may convert received audio data into an electrical signal and transmit the electrical signal to the speaker 251, and the speaker 251 converts the electrical signal into a sound signal for output. Additionally, the microphone 252 converts a collected sound signal into an electrical signal, and the audio circuit 250 receives the electrical signal, converts the electrical signal into audio data, and then outputs the audio data to the RF circuit 210, to send the audio data to, for example, another mobile phone, or outputs the audio data to the memory 220 for further processing.

Wi-Fi belongs to a short-range wireless transmission technology. With the Wi-Fi module 260, the mobile phone 200 can help the user receive and send e-mails, browse a web page, access streaming media, and the like. The Wi-Fi module 260 provides wireless broadband Internet access for the user. Although FIG. 2 shows the Wi-Fi module 260, it may be understood that the Wi-Fi module 260 is not a mandatory component of the mobile phone 200, and may be omitted as required without changing the essence of the present invention.

The processor 240 runs the software program and the module that are stored in the memory 220, to execute function applications and data processing of the mobile phone 200. The processor 240 is a control center of the mobile phone 200, and is connected to parts of the mobile phone by using interfaces and lines. By running or executing the software program and/or the module stored in the memory 220, and invoking the data stored in the memory 220, the processor 240 performs functions and data processing of the mobile phone 200, to perform overall monitoring on the mobile phone. Optionally, the processor 240 may include one or more processing units. The processor 240 may be integrated with an application processor and a modem processor. The application processor mainly processes the operating system, a user interface, the application program, and the like. The modem processor mainly processes the wireless communication. It may be understood that the modem processor may alternatively not be integrated into the processor 240. In addition, for the present invention, the processor may include a blur processing unit. The blur processing unit may be configured to: when the first to-be-detected item and the second to-be-detected item appear in a blurred state, delete images (the first image and the second image) corresponding to the blurred to-be-detected items (the first to-be-detected item and the second to-be-detected item), re-determine a first photographing parameter and the second photographing parameter, to acquire a new first image and a new second image; and determine detection results of the first to-be-detected item and the second to-be-detected item based on the re-acquired first image and second image. Alternatively, when the first to-be-detected item and the second to-be-detected item do not appear in a blurred state, the processor may detect the first image and the second image, to determine detection results of the first to-be-detected item and the second to-be-detected item, and determine a to-be-photographed range based on the first to-be-detected item and the second to-be-detected item that are captured by the camera.

The camera 280 includes a front-facing camera and a rear-facing camera. For the present invention, the camera 280 may be configured to acquire the first image and the second image, and may further adjust different focal lengths based on different photographing parameters. It should be noted that the camera 280 may be a camera fixed on the mobile phone, or may be a rotatable camera or a mobile camera, as described above. When the camera is a rotatable camera, the processor 240 determines the first to-be-detected item and the second to-be-detected item within a photographing range of the rotatable camera. When the first to-be-detected item and the second to-be-detected item are not within the photographing range, the processor 240 adjusts a position of the rotatable camera according to an instruction stored in the memory 220, so that the rotatable camera can photograph the first to-be-detected item and the second to-be-detected item.

The flash 290 may be configured to adjust, based on the first to-be-detected item and the second to-be-detected item, light intensities for photographing to-be-detected images. The flash may provide light for at least one of a flash mode, a flashlight mode, or a preset light emitting mode in a first mode or a second mode. It should be noted that lighting times in the flash mode, the flashlight mode, and the preset light emitting mode are different. For example, a lighting time in the flash mode is the shortest among the three modes, and lighting times in the flashlight mode and the preset light emitting mode are adjustable. Generally, a lighting time in the flashlight mode is longer than that in the preset light emitting mode. It should be noted that, when adjusting the light intensities for photographing the first image and the second image, the processor 240 may invoke an application program (for example, a flashlight application program) stored in the memory 220 to adjust the light intensities, or the processor 240 may drive an external LED light source and adjust light intensities and illumination times of the external LED light source.

The mobile phone 100 further includes the power supply 270 (for example, a battery) that supplies power to the components. The power supply may be logically connected to the processor 240 by using a power management system, to implement functions such as charging, discharging, and power consumption management by using the power management system.

Although not shown, the mobile phone 100 may further include a Bluetooth module and the like. Details are not described herein.

Figure 3:
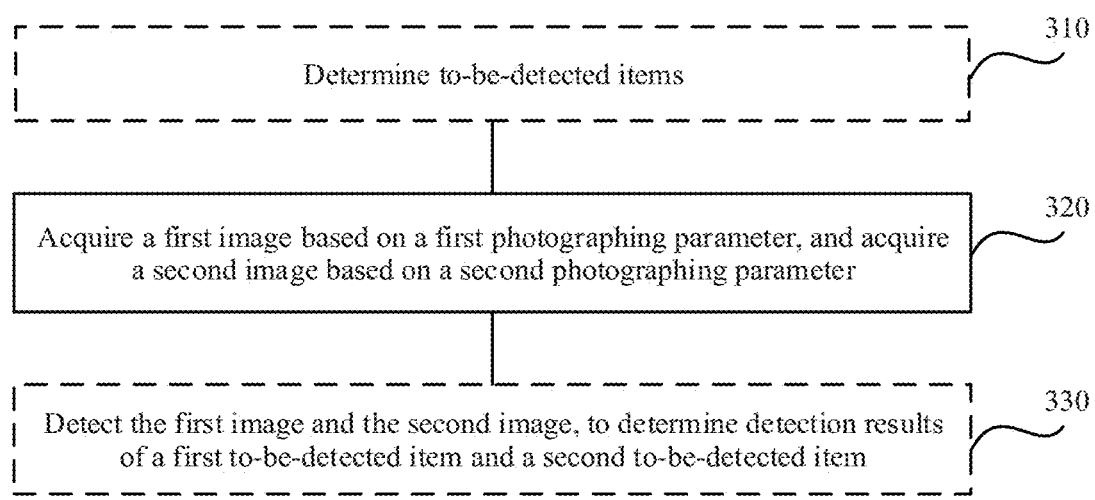
FIG. 3 is a schematic flowchart of an image acquisition method according to an embodiment of the present invention.

FIG. 3 is a schematic flowchart of an image processing method according to an embodiment of the present invention. As shown in FIG. 3, the method may include S310 to S330, as shown in the following.

S310. A terminal determines to-be-detected items, where the to-be-detected items may include a first to-be-detected item and a second to-be-detected item.

The first to-be-detected item and the second to-be-detected item may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis.

Preferably, the terminal determines the to-be-detected items based on a skin symptom type of a user. A first feature includes at least one of the following: the skin tone, the speckle, or the redness. The second feature includes at least one of the following: the acne, the oil content, the wrinkle, the eye feature, the blackhead, the water content, the melanin, the porphyrin, or the pore. The second to-be-detected item is classified into a third feature and a fourth feature based on a skin characteristic. The third feature includes at least one of the following: the blackhead, the eye feature, the melanin, the porphyrin, or the pore. The fourth feature includes at least one of the following: the skin tone, the speckle, the redness, the acne, the oil content, the wrinkle, or the water content. The eye feature includes at least one of the following: the under-eye puffiness, the under-eye dark circle, or the under-eye fine line. The wrinkle includes at least one of the nasolabial fold, the forehead wrinkle, the mountain root wrinkle, the upper lip wrinkle, or the downward wrinkle at the corner of the mouth. The water content includes at least one of the water content of epidermis or the water content of dermis.

Preferably, when the terminal meets a photographing condition, the terminal determines the to-be-detected items. The photographing condition includes an ambient light intensity and determining, by the terminal, that the to-be-detected items are within a photographing range.

For example, if the user wants to detect a skin status of a face of the user, the terminal needs to detect whether the terminal meets a photographing condition. If the photographing condition is met, S320 is performed. If the photographing condition is not met, the mobile phone (without a rotatable camera) needs to adjust a position, so that the to-be-detected items are within a photographing range of a camera of the mobile phone. Alternatively, when the camera of the mobile phone is a rotatable camera, the mobile phone adjusts a position of the rotatable camera based on a position of the face of the user or based on a position of the face of the user and an ambient light intensity, so that all to-be-detected items of the face of the user are within the photographing range of the camera of the mobile phone.

S320. The terminal acquires at least one first image based on a first photographing parameter, and acquires at least one second image based on a second photographing parameter, where the first image includes the first to-be-detected item, and the second image includes the second to-be-detected item.

The first photographing parameter includes a first light intensity and a first focal length, and the second photographing parameter includes a second light intensity and a second focal length. The terminal includes a light emitting diode LED light source, the LED light source emits light in a first mode to provide the first light intensity, and the LED light source emits light in a second mode to provide the second light intensity.

Preferably, the first mode includes at least one of a flashlight mode, a preset light emitting mode, or a flash mode, and the second mode includes at least one of the flashlight mode, the preset light emitting mode, or the flash mode. An operating current of the LED light source in the flashlight mode is a first current, and an operating current of the LED light source in the preset light emitting mode is a second current.

It should be noted that the user may autonomously select to use at least one of the flashlight mode, the preset light emitting mode, or the flash mode to perform photographing. Alternatively, the terminal may determine, based on the first to-be-detected item, to use at least one of the three modes to perform photographing, and determine, based on the second to-be-detected item, to use at least one of the three modes to perform photographing.

The determining, by the terminal, photographing modes based on the first detection item and the second detection item may include the following two possible implementations.

In a first possible implementation, there are any quantity of first to-be-detected items and second to-be-detected items, and the terminal determines, based on the first to-be-detected item, to acquire at least one first image by using at least one of the flashlight mode, the preset light emitting mode, or the flash mode. Focal lengths used to photograph all images in the at least one first image may be the same or may be different. Moreover, the terminal determines, based on the second to-be-detected item, to acquire at least one second image by using at least one of the flashlight mode, the preset light emitting mode, or the flash mode. Focal lengths used to photograph all images in the at least one second image may be the same or may be different. It should be noted that focal lengths used to photograph the first image and the second image are different.

In this possible implementation, for example:

The first to-be-detected item includes at least one of the skin tone, the speckle, or the redness, and the second to-be-detected item includes at least one of the blackhead, the eye feature, the melanin, the porphyrin, or the pore. The terminal determines, based on the first to-be-detected item, to use the flashlight mode in the first mode to perform photographing, to acquire three first images, and the terminal determines, based on the first to-be-detected item, to use the flash mode in the second mode to perform photographing, to acquire four second images.

In this possible implementation, for another example:

The first to-be-detected item includes at least one of the skin tone, the speckle, or the redness, and the second to-be-detected item includes at least one of the skin tone, the speckle, or the redness. The terminal determines, based on the first to-be-detected item, to use the flashlight mode in the first mode to perform photographing, to acquire three first images, and the terminal determines, based on the first to-be-detected item, to use the flash mode in the second mode to perform photographing, to acquire four second images. In this manner, the first to-be-detected item and the second to-be-detected item are the same, but different light intensities, lighting times, and focal lengths are used, and therefore finally presented first images and second images are different. In other words, even for a same detection item, images acquired by photographing by using different photographing parameters are different. Specifically, it may be understood that blur degrees of different depth-of-field positions and detail clarity degrees are different. Alternatively, it may be understood that the terminal may perceive a position of the same to-be-detected item from a plurality of aspects in the first images and the second images. For example, if the to-be-detected item includes the acne, and the acne is distributed at a joint between a nose and a cheek and on the cheek, by acquiring, by using different light intensities and different focal lengths, a plurality of first images and second images that display the acne, a more accurate position and size of the acne can be obtained from the plurality of first images and second images. Then, a detection result of the to-be-detected item is obtained by performing comprehensive processing on the same to-be-detected item in the plurality of first images and second images. This process can improve accuracy very well. A manner for comprehensive processing on the same to-be-detected item in the plurality of first images and second images may include at least one of the following: obtaining an average value, a maximum value, a minimum value, or a median value of the plurality of first images and second images.

In a second possible implementation, there are any quantity of first to-be-detected items and second to-be-detected items, and the terminal determines, based on the first to-be-detected item and the second to-be-detected item, to acquire only at least one first image by using at least one of the flashlight mode, the preset light emitting mode, or the flash mode in the first mode. Focal lengths used to photograph all images in the at least one first image may be the same or may be different. Alternatively, the terminal determines, based on the first to-be-detected item and the second to-be-detected item, to acquire only at least one second image by using at least one of the flashlight mode, the preset light emitting mode, or the flash mode in the second mode. Focal lengths used to photograph all images in the at least one second image may be the same or may be different.

In this possible implementation, for example:

The first to-be-detected item includes at least one of the skin tone, the speckle, or the redness, and the second to-be-detected item includes at least one of the blackhead, the eye feature, the melanin, the porphyrin, or the pore. The terminal determines, based on the first to-be-detected item and the second to-be-detected item, to use the flashlight mode in the first mode to perform photographing, to acquire five first images. In this case, the first to-be-detected item and the to-be-detected item in the images use the same mode, that is, the flashlight mode. The five first images appear to have a same light intensity and a same focal length. Such a manner may be implemented.

It should be noted that the foregoing three possible implementations are also applicable to the following embodiments.

In addition, a manner of determining the first focal length (a focal length used to acquire the first image) and the second focal length (a focal length used to acquire the second image) includes at least one of point focusing, area focusing, or full-body focusing. It should be noted that, because different focal lengths (the first focal length and the second focal length) and different light intensities (the first light intensity and the second light intensity) are used, object blur degrees of different depth of field positions and object detail clarity degrees in the first image and the second image are different. The different focal lengths correspond to the object blur degrees of the different depths of field positions, and the different light intensities correspond to the different object detail clarity degrees. In addition, all photographing processes of the method are subject to fully automatic continuous photographing, so that a user does not need to manually adjust a focal length and a light intensity, thereby improving user experience. Therefore, in this embodiment of the present invention, a plurality of to-be-detected images (the first image and the second image) are photographed in a plurality of photographing modes (the first photographing parameter and the second photographing parameter, where it should be noted that the first mode selected for the first photographing parameter may be the same as or different from the second mode selected for the second photographing parameter) for at least one to-be-detected item (the first to-be-detected item and the second to-be-detected item, where it should be noted that the first to-be-detected item and the second to-be-detected item may be the same or may be different). Arbitrary combination may be performed, thereby improving user satisfaction. (For example, three to-be-detected images are photographed in the flash mode, and to-be-detected items are the blackhead and the speckle. Moreover, five to-be-detected images are photographed in the flashlight mode, and to-be-detected items are the blackhead and the wrinkle. The terminal acquires a total of eight to-be-detected images, and detects three items. During display to the user, the terminal may show that the terminal has photographed the eight to-be-detected images, and has detected the three items. Alternatively, three to-be-detected images are photographed in the flash mode, and only one to-be-detected item is detected, which is the blackhead. In addition, five to-be-detected images are photographed in the flashlight mode, and the to-be-detected item "blackhead" is still detected. The terminal acquires a total of eight to-be-detected images, and detects the one item.)

Optionally, S330. The terminal detects the first image and the second image, to determine detection results of the first to-be-detected item and the second to-be-detected item.

In a possible implementation, the terminal detects the first image and the second image, to separately determine the detection results of the first to-be-detected item and the second to-be-detected item. The first image includes the first to-be-detected item, and the second image includes the second detection item.

In another possible implementation, the terminal synthesizes the first image and the second image to determine a to-be-detected image; and detects the to-be-detected image, to determine the detection results corresponding to the first to-be-detected item and the second to-be-detected item.

In addition, it should be noted that in step 330, the "determining, by the terminal, detection results of the first to-be-detected item and the second to-be-detected item based on a to-be-detected image" may specifically include the following steps.

Step 1: When the terminal detects that the first to-be-detected item or the second to-be-detected item is in a blurred state (that is, being invalid and unavailable), the terminal performs at least one of deleting at least one first image corresponding to the first to-be-detected item in a blurred state, or deleting at least one second image corresponding to the second to-be-detected item in a blurred state.

It should be noted that there may be at least one first to-be-detected item or second to-be-detected item in a blurred state. The following uses six examples for description:

A first possibility is: When one first to-be-detected item is in a blurred state, the one first to-be-detected item may be on one first image or may be on a plurality of first images. Therefore, the terminal deletes, based on the one first to-be-detected item in a blurred state, the one first image corresponding to the first to-be-detected item or the plurality of first images including the first to-be-detected item in a blurred state.

A second possibility is: When a plurality of first to-be-detected items are in a blurred state, the plurality of first to-be-detected items may appear on one first image, or may be distributed on a plurality of first images. Therefore, the terminal deletes, based on the plurality of first to-be-detected items in a blurred state, the one or more first images corresponding to the plurality of first to-be-detected items.

A third possibility is: When one second to-be-detected item is in a blurred state, the one second to-be-detected item may be on one second image or may be on a plurality of second images. Therefore, the terminal deletes, based on the one second to-be-detected item in a blurred state, the one second image corresponding to the second to-be-detected item or the plurality of second images including the second to-be-detected item in a blurred state.

A fourth possibility is: When a plurality of second to-be-detected items are in a blurred state, the plurality of second to-be-detected items may appear on one second image, or may be distributed on a plurality of second images. Therefore, the terminal deletes, based on the plurality of second to-be-detected items in a blurred state, the one or more second images corresponding to the plurality of second to-be-detected items.

A fifth possibility is: When a first to-be-detected item and a second to-be-detected item are in a blurred state, and the first to-be-detected item and the second to-be-detected item are a same to-be-detected item (for example, the acne), the terminal deletes at least one first image and at least one second image that correspond to the to-be-detected item. In other words, any image including a blurred to-be-detected item (for example, the acne) is deleted regardless of whether the image is a first image or a second image. It should be noted that in this case, there may be a plurality of first to-be-detected items and second to-be-detected items in a blurred state, provided that the first to-be-detected items and the second to-be-detected items in a blurred state are same to-be-detected items.

A sixth possibility is: When a first to-be-detected item and a second to-be-detected item are in a blurred state, and the first to-be-detected item and the second to-be-detected item are different to-be-detected items (for example, the first to-be-detected item is the acne, and the second to-be-detected item is the pore), the terminal deletes at least one first image corresponding to the first to-be-detected item, and deletes at least one second image corresponding to the second to-be-detected item. It should be noted that there may be a plurality of first to-be-detected items and second to-be-detected items in a blurred state.

Step 2: The terminal re-determines at least one of the first photographing parameter or the second photographing parameter, to acquire at least one of a new first image or a new second image.

Specifically, the re-determining may be performed in at least one of the following two manners: the three modes included in the first mode in the first photographing parameter, or the three modes included in the second mode in the second photographing parameter. For example, if the blackhead photographed in the flash mode based on the first photographing parameter is in a blurred state, the terminal changes to the flashlight mode to perform photographing, to acquire a first image photographed in the flashlight mode. Alternatively, if the acne photographed in the flashlight light mode based on the second photographing parameter is in a blurred state, the terminal changes to the preset light emitting mode to perform photographing, to acquire a second image photographed in the preset light emitting mode. Alternatively, when the blackhead photographed in the flash mode based on the first photographing parameter is in a blurred state and the acne photographed in the flashlight mode based on the second photographing parameter is also in a blurred state, the terminal changes the first photographing parameter to the flashlight mode to perform photographing, to acquire a first image photographed in the flashlight mode, and the terminal changes the second photographing parameter to the preset light emitting mode to perform photographing, to acquire a second image photographed in the preset light emitting mode. It should be noted that, in this application, if an image photographed after the first photographing parameter is changed the first time is still in a blurred state, the terminal may cyclically change in a sequence of the flash mode, the flashlight mode, and the preset light emitting mode.

Step 3: The terminal determines a detection result of at least one of the first to-be-detected item or the second to-be-detected item based on at least one of the re-acquired first image or the re-acquired second image.

For example, the first image corresponding to the blackhead is acquired according to the changed-to flashlight mode, and a detection result of the blackhead is determined. Alternatively, the second image corresponding to the acne is acquired based on the changed-to preset light emitting mode, and a detection result of the acne is determined. Alternatively, the first image corresponding to the blackhead is acquired according to the changed-to flashlight mode, and a detection result of the blackhead is determined; and the second image corresponding to the acne is acquired based on the changed-to preset light emitting mode, and a detection result of the acne is determined.

In addition, the user may be prompted to move a position of the terminal, to acquire a clearer photo. For example, if the terminal photographs, in the flash mode, a to-be-detected image (at least one of a first image or a second image) corresponding to the blackhead, and three photographed to-be-detected images are all blurred and unavailable, the terminal selects a clear photo in five to-be-detected images photographed in the flashlight photographing mode. If the blackhead in to-be-detected images photographed in all the photographing modes is blurred and unavailable, the terminal does not output a detection result of the blackhead but performs re-photographing. Alternatively, the terminal prompts, in at least one of the following manners, the user to perform re-photographing: displaying a blurred part of the blackhead in a to-be-detected image, and displaying a wording "the blackhead at a ** part is blurred".

In addition, it should be noted that before step 330, modeling may be further performed on the determined first image and second image (the first image and the second image may be images on which blur processing is performed, or may be images on which no blur processing is performed).

When the terminal determines to enter a to-be-detected item modeling mode (which may include modeling models of the first to-be-detected item and the second to-be-detected item), S340 may include: detecting, by the terminal, the first image and the second image based on the modeling models of the first to-be-detected item and the second to-be-detected item, to determine the detection results of the first to-be-detected item and the second to-be-detected item. In other words, it may be understood that one to-be-detected item corresponds to one modeling model. The to-be-detected item modeling mode is used to adjust definitions of the to-be-detected items in the first image and the second image based on models trained based on a plurality of first images and second images corresponding to the to-be-detected items, so that the detection results determined in S330 are more accurate.

Before the terminal determines to enter the to-be-detected item modeling mode, the method may further include: determining whether the modeling models in the to-be-detected item modeling mode are invalid modeling models.

Preferably, when time intervals between a first moment and moments at which the modeling models are established are greater than a threshold, it is determined that the modeling models are invalid modeling models. The first moment is a moment at which the terminal invokes the modeling models.

When the models are invalid modeling models, the terminal photographs a first image and a first modeling image based on the first photographing parameter, where the first modeling image is used to establish a modeling model for the first to-be-detected image; and the terminal photographs a second image and a second modeling image based on the second photographing parameter, where the second modeling image is used to establish a modeling model for the second to-be-detected image.

When the models are not invalid modeling models, the terminal adjusts the to-be-detected items in the first image and the second image by using the modeling models.

Figure 4:
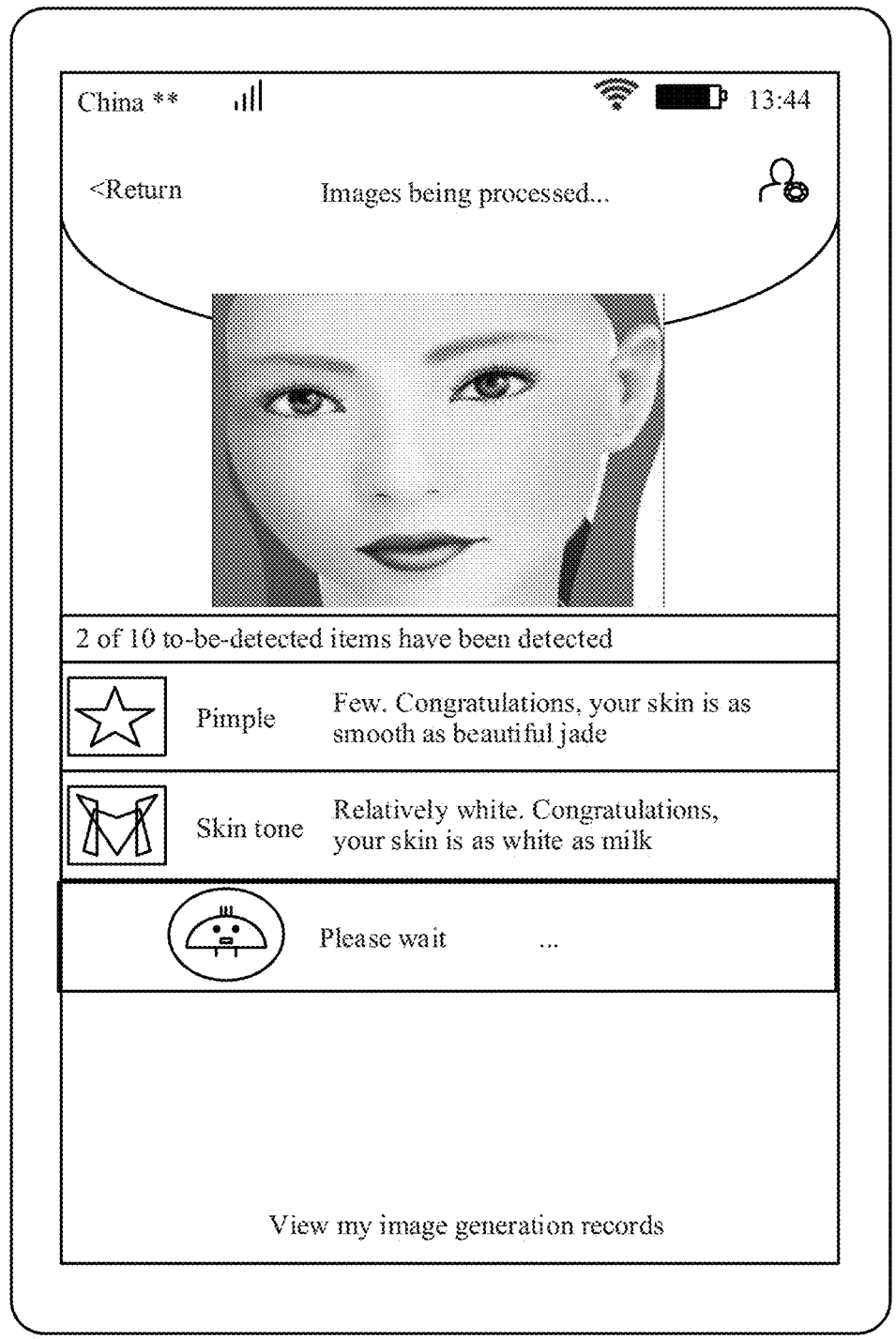
FIG. 4 is a schematic diagram of an interface in which skin care suggestions are generated based on detection results of to-be-detected items according to an embodiment of the present invention.

After the terminal performs the foregoing method steps, the method may further include:

generating, by the terminal based on the detection results of the to-be-detected items (the first to-be-detected item and the second to-be-detected item), skin care suggestions corresponding to the to-be-detected items, where the suggestions may be at least one of a voice prompt, a text prompt (for example, as shown in FIG. 4), or a video prompt. The skin care suggestions may be obtained by using big data, or may be provided by an online professional. A specific manner is not limited herein. In this embodiment, blur processing is performed, so that the obtained detection results can be more accurate, and user satisfaction can be improved during use by the user. The following further describes, with reference to FIG. 5 to FIG. 8, a multi-parameter image acquisition method according to an embodiment of the present invention.

Figure 5:
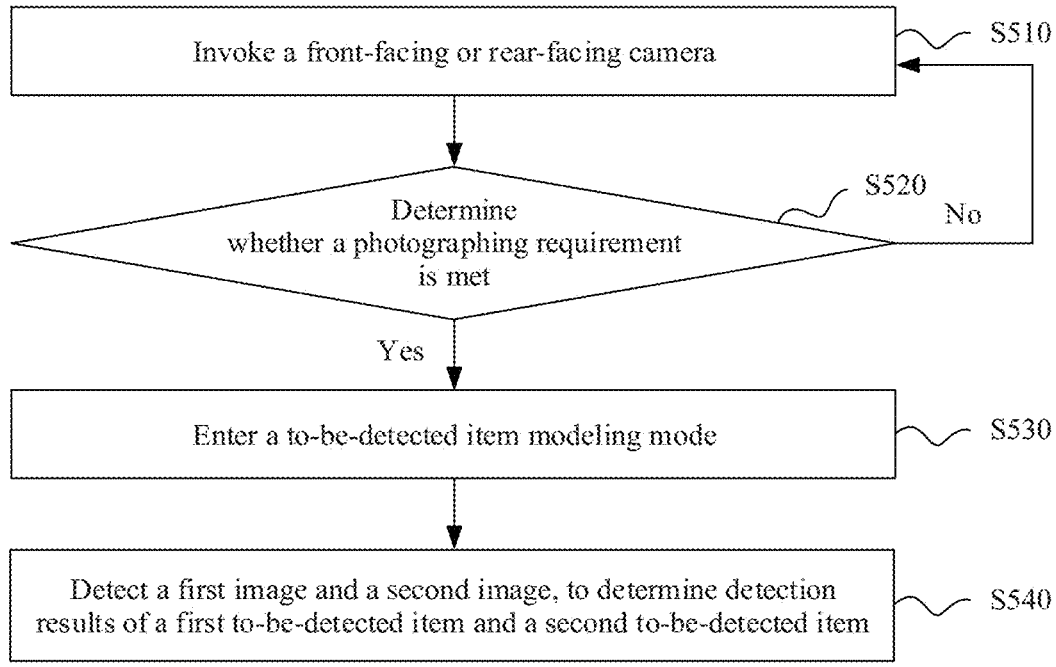
FIG. 5 is a flowchart of a multi-parameter image acquisition method according to an embodiment of the present invention.

FIG. 5 is a flowchart of a multi-parameter image acquisition method according to an embodiment of the present invention. As shown in FIG. 5, in this embodiment, the method does not have a blur processing process, but includes a modeling process, as shown in S510 to S540.

S510. A mobile phone invokes a front-facing or rear-facing camera to acquire to-be-detected items, where the to-be-detected items may include a first to-be-detected item and a second to-be-detected item.

S520. The mobile phone determines whether a photographing range of the camera meets a photographing condition. Preferably, focusing corresponding to the to-be-detected item is adjusted (which may be understood as adjusting a focal length). An ambient light intensity is read. If the ambient light intensity does not meet a light intensity for photographing, it is prompted to adjust a photographing angle. It should be noted that steps of adjusting the focal length and adjusting the light intensity may be exchanged. This is not limited in the present invention.

When the photographing condition is not met, the mobile phone (in this case, the mobile phone has a rotatable camera) adjusts a position of the rotatable camera based on positions of the to-be-detected items, so that all the to-be-detected items are within a photographing range of the camera. It should be noted that, when the mobile phone does not include a rotatable camera, a position of the mobile phone may be directly adjusted, so that all the to-be-detected items are within the photographing range of the camera.

S530. When determining that a photographing range of the camera meets a photographing requirement, the mobile phone enters a to-be-detected item modeling mode.

The to-be-detected item modeling mode includes modeling models of the to-be-detected items. The to-be-detected item modeling mode is used to adjust, based on to-be-detected image training models corresponding to a plurality of to-be-detected items, definitions of the to-be-detected items in to-be-detected images.

Before this step, the method may further include: determining whether the modeling models of the to-be-detected items are invalid models. Preferably, when time intervals between a first moment and moments at which the modeling models of the to-be-detected items are established are greater than a threshold, it is determined that the modeling models of the to-be-detected items are invalid modeling models. The first moment is a moment at which the terminal invokes the modeling models of the to-be-detected items.

If the models are not invalid models, S540 is performed.

If the models are invalid models, the mobile phone determines, based on photographing parameters corresponding to the to-be-detected items, a plurality of first images, second images, and modeling images corresponding to the to-be-detected items (in other words, it is determined which images are to-be-detected images and which images are modeling images). The modeling images are used to establish modeling models of the to-be-detected items.

There is also a possibility that the models are not invalid models, but when a quantity of modeling images in a modeling model corresponding to a to-be-detected item is lower than a preset threshold, in addition to a first image and a second image, the terminal needs to photograph sufficient modeling images during next photographing. The modeling images are not displayed to a user (this is a modeling-hidden solution, that is, which images are to-be-detected images and which images are modeling images are not clearly described. When the terminal detects that a background modeling model is lacked or is old and unavailable, the terminal automatically photographs sufficient modeling and to-be-detected images. Otherwise, the terminal photographs only to-be-detected images. The user perceives only that a quantity of photographed images is different each time, but at any time, detection results are obtained after photographing. After detection results are obtained each time, the terminal refreshes the background modeling model based on a newly photographed image (a modeling image) and a previous image (a modeling image). It should be noted that, preferably, a modeling model is updated by using a newly photographed image, to ensure that the modeling model changes with a face of a person. Certainly, the modeling model may alternatively be updated at a fixed time or a random time. This is not limited in the present invention.) In other words, the user is unaware of the modeling images. In this manner, a phase of acquiring a modeling image is added. In this phase, a modeling model may be established based on at least one modeling image. The background model may be a modeling model corresponding to a to-be-detected item described above.

S540. Detect a plurality of first images and second images respectively based on the modeling models of the to-be-detected items, to determine detection results of the to-be-detected items.

In the to-be-detected item modeling mode, a manner of photographing to-be-detected images based on the to-be-detected items may include the following manners:

In a possible implementation, the first to-be-detected item and the second to-be-detected item include a same to-be-detected item.

Preferably, a plurality of first images are photographed in a first mode based on a first photographing parameter, and a plurality of second images are photographed in a second mode based on a second photographing parameter; and the first to-be-detected item and the second to-be-detected item that are included in the plurality of first images (the first to-be-detected item and the second to-be-detected item include a same to-be-detected item) are identified. Modeling adjustment is performed on the same to-be-detected item based on a modeling model corresponding to the to-be-detected item, to obtain a clearer to-be-detected item. If there are a plurality of first to-be-detected items and the second to-be-detected item further includes to-be-detected items that are the same as the first to-be-detected items, the foregoing operations are repeated, until all to-be-detected items are adjusted by using modeling models. A detection result is determined based on at least one to-be-detected item obtained after the adjustment. It should be noted that sub-modes (for example, at least one of a flashlight mode, a flash mode, or a preset light emitting mode) selected in the first mode and the second mode may be the same, or may be different.

The foregoing statement is described by using an example. For example, three first to-be-detected images are acquired in the flash mode in the first mode corresponding to the first photographing parameter, and first to-be-detected items in the first to-be-detected images are a blackhead and acne. Three second to-be-detected images are acquired in the flashlight mode in the second mode corresponding to the second photographing parameter, and second to-be-detected items in the second to-be-detected image are the blackhead and the acne. The terminal acquires a total of eight to-be-detected images, and detects two to-be-detected items. The terminal adjusts the detected two to-be-detected items by using pre-stored modeling models respectively corresponding to the two to-be-detected items.

In another possible implementation, the first to-be-detected item and the second to-be-detected item include different to-be-detected items.

Preferably, a plurality of first images are photographed in the first mode based on the first photographing parameter, and a plurality of second images are photographed in the second mode based on the second photographing parameter; and the first to-be-detected item and the second to-be-detected item that are included in the plurality of first images (the first to-be-detected item and the second to-be-detected item include different to-be-detected items) are identified. Modeling adjustment is performed on different to-be-detected items based on modeling models corresponding to the to-be-detected items, to acquire clearer to-be-detected items. If there may be a plurality of first to-be-detected items and a plurality of second to-be-detected items, the foregoing operations are repeated, until all to-be-detected items are adjusted by using modeling models. A detection result is determined based on at least one to-be-detected item obtained after the adjustment. It should be noted that sub-modes (for example, at least one of a flashlight mode, a flash mode, or a preset light emitting mode) selected in the first mode and the second mode may be the same, or may be different.

The foregoing statement is described by using an example. For example, three first to-be-detected images are acquired in the flash mode in the first mode corresponding to the first photographing parameter, and first to-be-detected items in the first to-be-detected images are a blackhead and acne. Three second to-be-detected images are acquired in the flashlight mode in the second mode corresponding to the second photographing parameter, and second to-be-detected items in the second to-be-detected image are a speckle and a wrinkle. The terminal acquires a total of eight to-be-detected images, and detects four to-be-detected items. The terminal adjusts the detected four to-be-detected items by using pre-stored modeling models respectively corresponding to the four to-be-detected items.

In another possible implementation, the first to-be-detected item and the second to-be-detected item include a same to-be-detected item and different to-be-detected items.

Preferably, a plurality of first images are photographed in the first mode based on the first photographing parameter, and a plurality of second images are photographed in the second mode based on the second photographing parameter;

and the first to-be-detected item and the second to-be-detected item that are included in the plurality of first images (the first to-be-detected item and the second to-be-detected item include a same to-be-detected item and different to-be-detected items) are identified. Modeling adjustment is performed on different to-be-detected items based on modeling models corresponding to the to-be-detected items, to acquire clearer to-be-detected items. If there may be a plurality of first to-be-detected items and a plurality of second to-be-detected items, the foregoing operations are repeated, until all to-be-detected items are adjusted by using modeling models. A detection result is determined based on at least one to-be-detected item obtained after the adjustment. It should be noted that sub-modes (for example, at least one of a flashlight mode, a flash mode, or a preset light emitting mode) selected in the first mode and the second mode may be the same, or may be different.

The foregoing statement is described by using an example. For example, three first to-be-detected images are acquired in the flash mode in the first mode corresponding to the first photographing parameter, and first to-be-detected items in the first to-be-detected images are a blackhead and acne. Three second to-be-detected images are acquired in the flashlight mode in the second mode corresponding to the second photographing parameter, and second to-be-detected items in the second to-be-detected image are the blackhead and a wrinkle. The terminal acquires a total of eight to-be-detected images, and detects three to-be-detected items. The terminal adjusts the detected three to-be-detected items by using pre-stored modeling models respectively corresponding to the three to-be-detected items.

It should be noted that, when there are a plurality of first images and second images as described above, the step of determining detection results of the to-be-detected items may specifically include: determining, by obtaining an average value, a maximum value, a minimum value, or a median value of the plurality of first images and second images, the detection results corresponding to the to-be-detected items.

In the foregoing manner, a plurality of to-be-detected images (the first image and the second image) are determined based on a plurality of photographing modes (the first mode and the second mode) corresponding to at least one to-be-detected item (the first to-be-detected item and the second to-be-detected item), to determine a measurement result corresponding to the to-be-detected item. In this manner, a to-be-detected item in to-be-detected images is determined from a plurality of angles by using different photographing modes during skin health detection, to obtain a more accurate detection result.

In the foregoing manner, a more stable and accurate measurement result is obtained through modeling, and different modeling models are set based on different to-be-detected items during skin health detection to adjust different the to-be-detected items, so that more accurate detection results are obtained.

Figure 6:
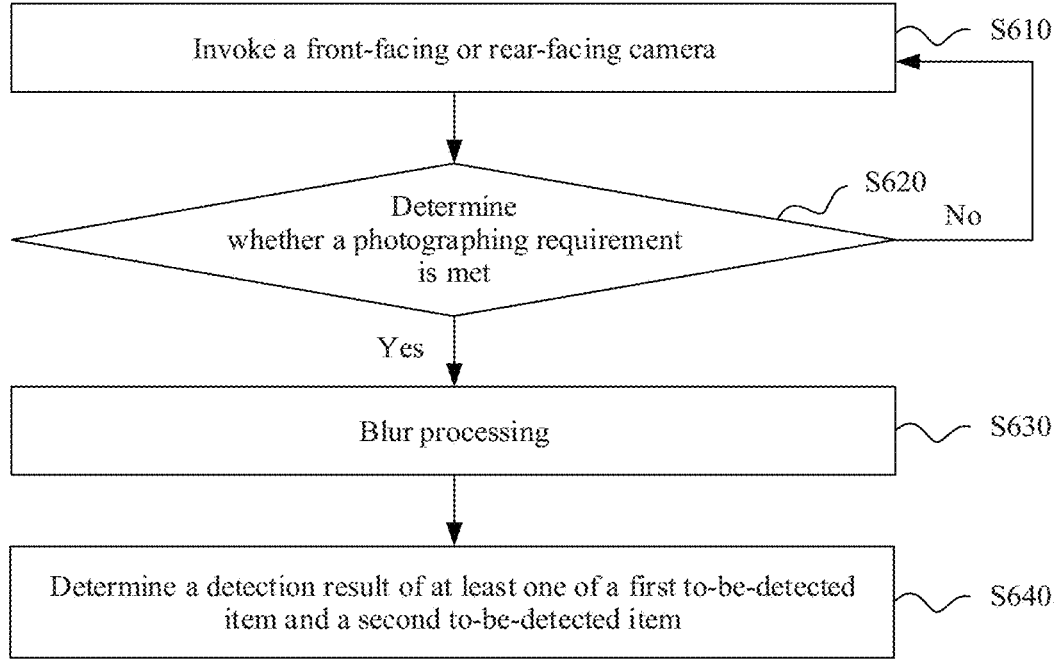
FIG. 6 is a flowchart of another multi-parameter image acquisition method according to an embodiment of the present invention.

FIG. 6 is a flowchart of another multi-parameter image acquisition method according to an embodiment of the present invention. As shown in FIG. 6, in this embodiment, the method includes blur processing, but does not have a modeling model, as shown in S610 to S640.

S610 and S620 are the same as S510 and S520 shown in FIG. 5. Therefore, details are not described herein again.

S630. The mobile phone enters a processing mode.

Specifically, when the mobile phone detects that the first to-be-detected item or the second to-be-detected item is in a blurred state (that is, being invalid and unavailable), the mobile phone performs at least one of deleting at least one first image corresponding to the first to-be-detected item in a blurred state, or deleting at least one second image corresponding to the second to-be-detected item in a blurred state.

It should be noted that there may be at least one first to-be-detected item or second to-be-detected item in a blurred state. The following uses six examples for description:

A first possibility is: When one first to-be-detected item is in a blurred state, the one first to-be-detected item may be on one first image or may be on a plurality of first images. Therefore, the mobile phone deletes, based on the one first to-be-detected item in a blurred state, the one first image corresponding to the first to-be-detected item or the plurality of first images including the first to-be-detected item in the blurred state.

A second possibility is: When a plurality of first to-be-detected items are in a blurred state, the plurality of first to-be-detected items may appear on one first image, or may be distributed on a plurality of first images. Therefore, the mobile phone deletes, based on the plurality of first to-be-detected items in a blurred state, the one or more first images corresponding to the plurality of first to-be-detected items.

A third possibility is: When one second to-be-detected item is in a blurred state, the one second to-be-detected item may be on one second image or may be on a plurality of second images. Therefore, the mobile phone deletes, based on the one second to-be-detected item in a blurred state, the one second image corresponding to the second to-be-detected item or the plurality of second images including the second to-be-detected item in the blurred state.

A fourth possibility is: When a plurality of second to-be-detected items are in a blurred state, the plurality of second to-be-detected items may appear on one second image, or may be distributed on a plurality of second images. Therefore, the mobile phone deletes, based on the plurality of second to-be-detected items in a blurred state, the one or more second images corresponding to the plurality of second to-be-detected items.

A fifth possibility is: When a first to-be-detected item and a second to-be-detected item are in a blurred state, and the first to-be-detected item and the second to-be-detected item are a same to-be-detected item (for example, acne), the mobile phone deletes at least one first image and at least one second image that correspond to the to-be-detected item. In other words, any image including a blurred to-be-detected item (for example, acne) is deleted regardless of whether the image is a first image or a second image. It should be noted that in this case, there may be a plurality of first to-be-detected items and second to-be-detected items in a blurred state, provided that the first to-be-detected items and the second to-be-detected items in a blurred state are same to-be-detected items.

A sixth possibility is: When a first to-be-detected item and a second to-be-detected item are in a blurred state, and the first to-be-detected item and the second to-be-detected item are different to-be-detected items (for example, the first to-be-detected item is acne, and the second to-be-detected item is a pore), the mobile phone deletes at least one first image corresponding to the first to-be-detected item, and deletes at least one second image corresponding to the second to-be-detected item. It should be noted that there may be a plurality of first to-be-detected items and second to-be-detected items in a blurred state.

The mobile phone re-determines at least one of the first photographing parameter or the second photographing parameter, to acquire at least one of a new first image or a new second image.

Specifically, the re-determining may be performed in at least one of the following two manners: the three modes included in the first mode in the first photographing parameter, or the three modes included in the second mode in the second photographing parameter. For example, a blackhead photographed in the flash mode based on the first photographing parameter is in a blurred state, the mobile phone changes to the flashlight mode to perform photographing, to acquire a first image photographed in the flashlight mode. Alternatively, if acne photographed in the flashlight light mode based on the second photographing parameter is in a blurred state, the mobile phone changes to the preset light emitting mode to perform photographing, to acquire a second image photographed in the preset light emitting mode. Alternatively, when a blackhead photographed in the flash mode based on the first photographing parameter is in a blurred state and acne photographed in the flashlight mode based on the second photographing parameter is also in a blurred state, the mobile phone changes the first photographing parameter to the flashlight mode to perform photographing, to acquire a first image photographed in the flashlight mode, and the mobile phone changes the second photographing parameter to the preset light emitting mode to perform photographing, to acquire a second image photographed in the preset light emitting mode. It should be noted that, in this application, if an image photographed after the first photographing parameter is changed the first time is still in a blurred state, the terminal may cyclically change in a sequence of the flash mode, the flashlight mode, and the preset light emitting mode.

S640. The mobile phone determines a detection result of at least one of the first to-be-detected item or the second to-be-detected item based on at least one of the re-acquired first image or the re-acquired second image.

For example, the first image corresponding to the blackhead is acquired according to the changed-to flashlight mode, and a detection result of the blackhead is determined. Alternatively, the second image corresponding to the acne is acquired based on the changed-to preset light emitting mode, and a detection result of the acne is determined. Alternatively, the first image corresponding to the blackhead is acquired according to the changed-to flashlight mode, and a detection result of the blackhead is determined; and the second image corresponding to the acne is acquired based on the changed-to preset light emitting mode, and a detection result of the acne is determined.

In addition, the user may be prompted to move a position of the mobile phone, to acquire a clearer photo. For example, if the mobile phone photographs, in the flash mode, a to-be-detected image (at least one of a first image or a second image) corresponding to the blackhead, and three photographed to-be-detected images are all blurred and unavailable, the mobile phone selects a clear photo in five to-be-detected images photographed in the flashlight photographing mode. If the blackhead in to-be-detected images photographed in all the photographing modes is blurred and unavailable, the mobile phone does not output a detection result of the blackhead but performs re-photographing. Alternatively, the mobile phone prompts, in at least one of the following manners, the user to perform re-photographing: displaying a blurred part of the blackhead in a to-be-detected image, and displaying a wording "the blackhead at a ** part is blurred".

Figure 7:
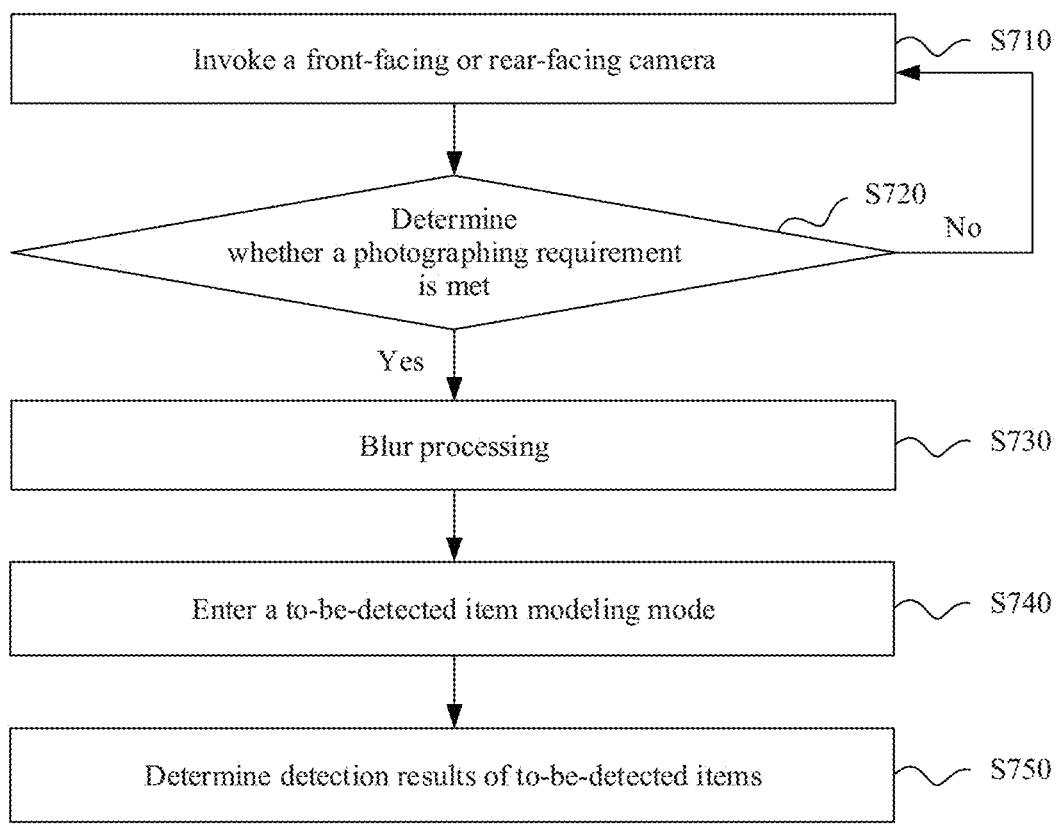
FIG. 7 is a flowchart of still another multi-parameter image acquisition method according to an embodiment of the present invention.

FIG. 7 is a flowchart of still another multi-parameter image acquisition method according to an embodiment of the present invention. As shown in FIG. 7, in this embodiment, the method includes blur processing and a modeling model, as shown in S710 to S740.

S710 and S720 are the same as S510 and S520 shown in FIG. 5. Therefore, details are not described herein again.

S730 is the same as S630 in FIG. 6. Therefore, details are not described herein again.

S740. The mobile phone enters a to-be-detected item modeling mode.

Specifically, the to-be-detected item modeling mode includes modeling models of the to-be-detected items. The to-be-detected item modeling mode is used to adjust, based on to-be-detected image training models corresponding to a plurality of to-be-detected items, definitions of the to-be-detected items in to-be-detected images.

Before this step, the method may further include: determining whether the modeling models of the to-be-detected items are invalid models. Preferably, when time intervals between a first moment and moments at which the modeling models of the to-be-detected items are established are greater than a threshold, it is determined that the modeling models of the to-be-detected items are invalid modeling models. The first moment is a moment at which the terminal invokes the modeling models of the to-be-detected items.

If the models are not invalid models, the models are directly used to perform corresponding detection on the to-be-detected items.

If the models are invalid models, the mobile phone determines, based on photographing parameters corresponding to the to-be-detected items, a plurality of first images, second images, and modeling images corresponding to the to-be-detected items. The modeling images are used to establish modeling models of the to-be-detected items.

There is also a possibility that the models are not invalid models, but when a quantity of modeling images in a modeling model corresponding to a to-be-detected item is lower than a preset threshold, in addition to a first image and a second image, the terminal needs to photograph sufficient modeling images during next photographing. The modeling images are not displayed to a user. In other words, the user is unaware of the modeling images. In this manner, a phase of acquiring a modeling image is added. In this phase, a modeling model may be established based on at least one modeling image. The background model may be a modeling model corresponding to a to-be-detected item described above.

S750. The mobile phone detects a plurality of to-be-detected images, to determine detection results of the to-be-detected items (the first to-be-detected item and the second to-be-detected item).

Specifically, in the to-be-detected item modeling mode, a manner of photographing to-be-detected images based on the to-be-detected items may include the following manners:

In a possible implementation, the first to-be-detected item and the second to-be-detected item include a same to-be-detected item.

Preferably, a plurality of first images are photographed in a first mode based on a first photographing parameter, and a plurality of second images are photographed in a second mode based on a second photographing parameter; and the first to-be-detected item and the second to-be-detected item that are included in the plurality of first images (the first to-be-detected item and the second to-be-detected item include a same to-be-detected item) are identified. Modeling adjustment is performed on the same to-be-detected item based on a modeling model corresponding to the to-be-detected item, to obtain a clearer to-be-detected item. If there are a plurality of first to-be-detected items and the second to-be-detected item further includes to-be-detected items that are the same as the first to-be-detected items, the foregoing operations are repeated, until all to-be-detected items are adjusted by using modeling models. A detection result is determined based on at least one to-be-detected item obtained after the adjustment. It should be noted that sub-modes (for example, at least one of a flashlight mode, a flash mode, or a preset light emitting mode) selected in the first mode and the second mode may be the same, or may be different.

The foregoing statement is described by using an example. For example, three first to-be-detected images are acquired in the flash mode in the first mode corresponding to the first photographing parameter, and first to-be-detected items in the first to-be-detected images are a blackhead and acne. Three second to-be-detected images are acquired in the flashlight mode in the second mode corresponding to the second photographing parameter, and second to-be-detected items in the second to-be-detected image are the blackhead and the acne. The terminal acquires a total of eight to-be-detected images, and detects two to-be-detected items. The terminal adjusts the detected two to-be-detected items by using pre-stored modeling models respectively corresponding to the two to-be-detected items.

In another possible implementation, the first to-be-detected item and the second to-be-detected item include different to-be-detected items.

Preferably, a plurality of first images are photographed in the first mode based on the first photographing parameter, and a plurality of second images are photographed in the second mode based on the second photographing parameter; and the first to-be-detected item and the second to-be-detected item that are included in the plurality of first images (the first to-be-detected item and the second to-be-detected item include different to-be-detected items) are identified. Modeling adjustment is performed on different to-be-detected items based on modeling models corresponding to the to-be-detected items, to acquire clearer to-be-detected items. If there may be a plurality of first to-be-detected items and a plurality of second to-be-detected items, the foregoing operations are repeated, until all to-be-detected items are adjusted by using modeling models. A detection result is determined based on at least one to-be-detected item obtained after the adjustment. It should be noted that sub-modes (for example, at least one of a flashlight mode, a flash mode, or a preset light emitting mode) selected in the first mode and the second mode may be the same, or may be different.

The foregoing statement is described by using an example. For example, three first to-be-detected images are acquired in the flash mode in the first mode corresponding to the first photographing parameter, and first to-be-detected items in the first to-be-detected images are a blackhead and acne. Three second to-be-detected images are acquired in the flashlight mode in the second mode corresponding to the second photographing parameter, and second to-be-detected items in the second to-be-detected image are a speckle and a wrinkle. The terminal acquires a total of eight to-be-detected images, and detects four to-be-detected items. The terminal adjusts the detected four to-be-detected items by using pre-stored modeling models respectively corresponding to the four to-be-detected items.

In another possible implementation, the first to-be-detected item and the second to-be-detected item include a same to-be-detected item and different to-be-detected items.

Preferably, a plurality of first images are photographed in the first mode based on the first photographing parameter, and a plurality of second images are photographed in the second mode based on the second photographing parameter; and the first to-be-detected item and the second to-be-detected item that are included in the plurality of first images (the first to-be-detected item and the second to-be-detected item include a same to-be-detected item and different to-be-detected items) are identified. Modeling adjustment is performed on different to-be-detected items based on modeling models corresponding to the to-be-detected items, to acquire clearer to-be-detected items. If there may be a plurality of first to-be-detected items and a plurality of second to-be-detected items, the foregoing operations are repeated, until all to-be-detected items are adjusted by using modeling models. A detection result is determined based on at least one to-be-detected item obtained after the adjustment. It should be noted that sub-modes (for example, at least one of a flashlight mode, a flash mode, or a preset light emitting mode) selected in the first mode and the second mode may be the same, or may be different.

The foregoing statement is described by using an example. For example, three first to-be-detected images are acquired in the flash mode in the first mode corresponding to the first photographing parameter, and first to-be-detected items in the first to-be-detected images are a blackhead and acne. Three second to-be-detected images are acquired in the flashlight mode in the second mode corresponding to the second photographing parameter, and second to-be-detected items in the second to-be-detected image are the blackhead and a wrinkle. The terminal acquires a total of eight to-be-detected images, and detects three to-be-detected items. The terminal adjusts the detected three to-be-detected items by using pre-stored modeling models respectively corresponding to the three to-be-detected items.

It should be noted that, when there are a plurality of first images and second images as described above, the step of determining detection results of the to-be-detected items may specifically include: determining, by obtaining an average value, a maximum value, a minimum value, or a median value of the plurality of first images and second images, the detection results corresponding to the to-be-detected items.

Figure 8:
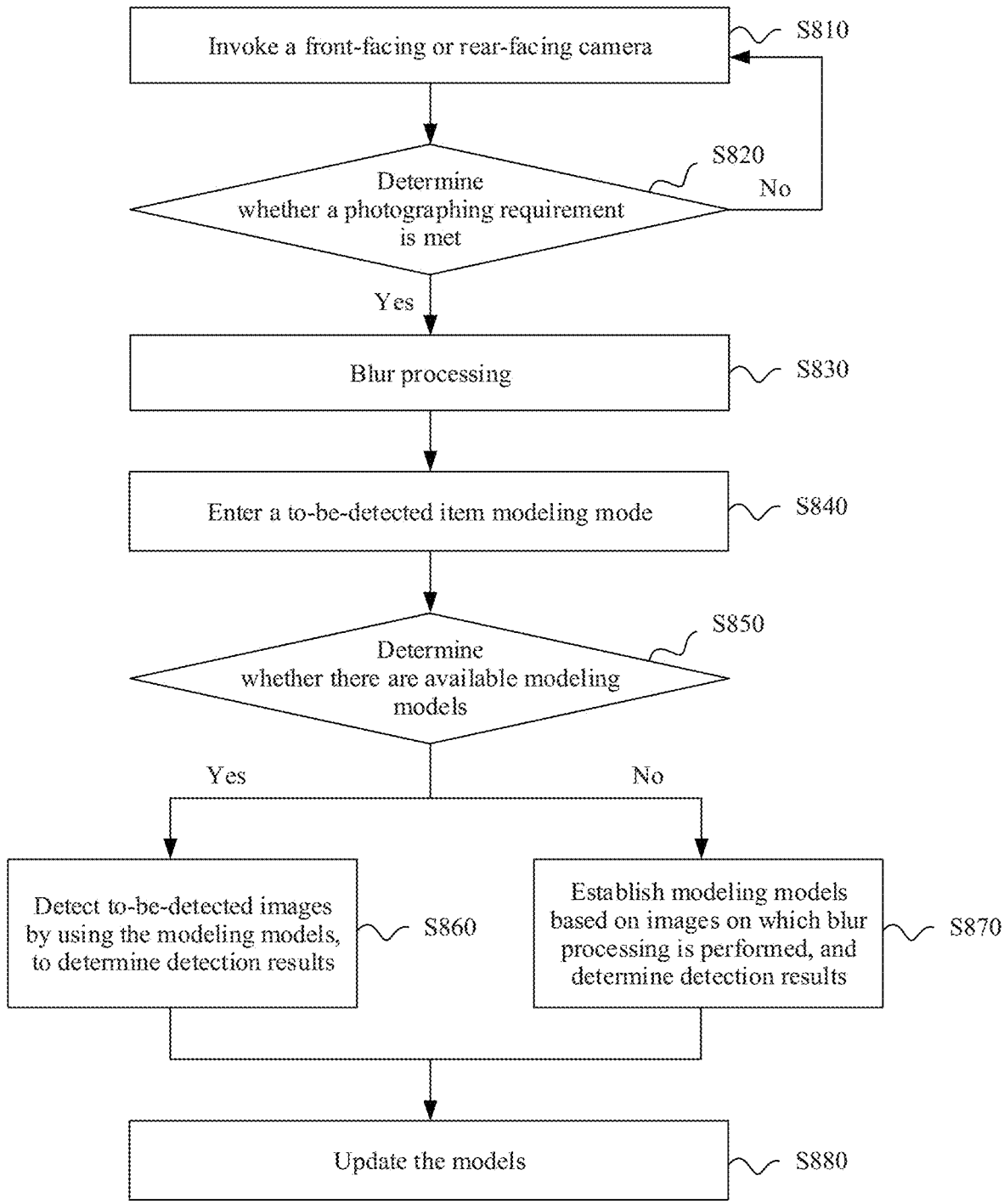
FIG. 8 is a flowchart of still another multi-parameter image acquisition method according to an embodiment of the present invention.

FIG. 8 is a flowchart of still another multi-parameter image acquisition method according to an embodiment of the present invention. As shown in FIG. 8, in this embodiment, the method also includes blur processing and a modeling model, as shown in S810 to S880.

S810 to S840 are the same as S710 to S740 shown in FIG. 7. Therefore, details are not described herein again.

S850. Determine whether there are modeling models available for the to-be-detected items.

If there are available modeling models, S860. Detect the to-be-detected items in to-be-detected images by using the modeling models, to determine detection results of the to-be-detected items.

If there are no available modeling models, S870. Determine a plurality of to-be-detected items based on images on which the blur processing is performed, establish modeling models based on the plurality of detection items, and detect the to-be-detected items in to-be-detected images by using the newly established modeling models, to determine detection results of the to-be-detected items. It should be noted that a modeling process may be understood as assuming that a to-be-detected item in an image on which the blur processing is performed is selected, and forming a new modeling model by using the to-be-detected item and latest data in a model. For example, a ratio of the two may be 5:5 or 4:6.

S880. The mobile phone updates the modeling models based on the detection results obtained by using the modeling models.

Figure 9:
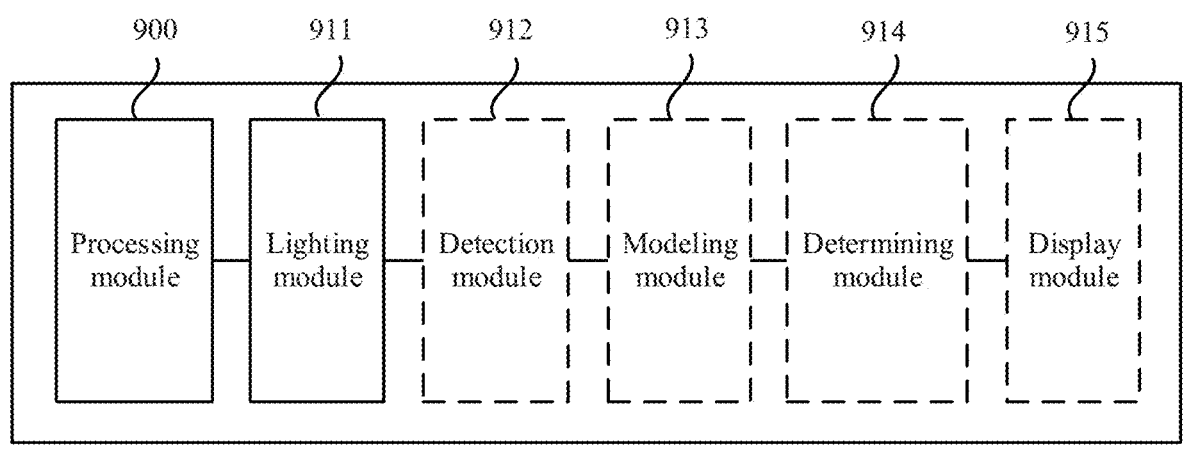
FIG. 9 is a structural flowchart of an image acquisition apparatus according to an embodiment of the present invention.

FIG. 9 is a structural flowchart of an image processing apparatus according to an embodiment of the present invention. As shown in FIG. 9, the apparatus may include a processing module 900, which may be configured to acquire at least one first image based on a first photographing parameter, where the first image includes a first to-be-detected item; and acquire at least one second image based on a second photographing parameter, where the second image includes a second to-be-detected item, the first photographing parameter includes a first light intensity and a first focal length, and the second photographing parameter includes a second light intensity and a second focal length; and a lighting module 911, where the lighting module 911 may include a light emitting diode LED light source, the LED light source is configured to emit light in a first mode to provide the first light intensity, and the LED light source emits light in a second mode to provide the second light intensity.

The first mode may include at least one of a flashlight mode, a preset light emitting mode, or a flash mode, an operating current of the LED light source in the flashlight mode is a first current, and an operating current of the LED light source in the preset light emitting mode is a second current. The second mode may include at least one of the flashlight mode, the preset light emitting mode, or the flash mode. Light intensities and lighting times in the flashlight mode and the preset light emitting mode are adjustable. A manner of adjusting the "first focal length" and the "second focal length" includes at least one of point focusing, area focusing, or full-face focusing.

The processing module may be specifically configured to: when the apparatus meets a photographing condition, acquire at least one first image based on the first photographing parameter, and acquire at least two second images based on the second photographing parameter, where the photographing condition includes an ambient light intensity and determining, by the apparatus, that the first to-be-detected item and the second to-be-detected item are within a photographing range.

The first to-be-detected item and the second to-be-detected item may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis.

Specifically, the first to-be-detected item may be classified into a first feature and a second feature based on a skin characteristic. The first feature includes at least one of the following: the skin tone, the speckle, or the redness. The second feature includes at least one of the following: the acne, the oil content, the wrinkle, the eye feature, the blackhead, the water content, the melanin, the porphyrin, or the pore. The second to-be-detected item may be classified into a third feature and a fourth feature based on a skin characteristic. The third feature includes at least one of the following: the blackhead, the eye feature, the melanin, the porphyrin, or the pore. The fourth feature includes at least one of the following: the skin tone, the speckle, the redness, the acne, the oil content, the wrinkle, or the water content. The eye feature includes at least one of the following: the under-eye puffiness, the under-eye dark circle, or the under-eye fine line. The wrinkle includes at least one of the following: the nasolabial fold, the forehead wrinkle, the mountain root wrinkle, the upper lip wrinkle, or the downward wrinkle at the corner of the mouth. The water content includes at least one of the following: the water content of epidermis or the water content of dermis.

The apparatus may further include a detection module 912, which may be configured to detect the first image and the second image, to determine detection results of the first to-be-detected item and the second to-be-detected item. The detection module may be specifically configured to detect the first image and the second image, to separately determine the detection results of the first to-be-detected item and the second to-be-detected item, where the first image includes the first to-be-detected item, and the second image includes the second detection item. The detection module may be specifically configured to: when there are a plurality of to-be-detected images, synthesize the to-be-detected images into one detection image, and determine the detection results of the first to-be-detected item and the second to-be-detected item based on the synthesized to-be-detected image. The detection module may be specifically configured to: when there are a plurality of to-be-detected images, detect each of the plurality of to-be-detected images, to determine detection results corresponding to the first to-be-detected item and the second to-be-detected item in each to-be-detected image; and synthesize detection results of all the images, to determine the detection results of the first to-be-detected item and the second to-be-detected item.

In addition, when at least one of the first to-be-detected item in the first image or the second to-be-detected item in the second image is in a blurred state, the detection module may be specifically configured to delete at least one of the first image or the second image; re-determine at least one of the first photographing parameter or the second photographing parameter, to acquire at least one of the first image or the second image; and determine a detection result of the at least one of the first to-be-detected item or the second to-be-detected item based on the at least one of the re-acquired first image or the re-acquired second image.

The apparatus may further include a modeling module 913, which may be configured to determine to enter a to-be-detected item modeling mode, where the to-be-detected item modeling mode includes modeling models for detecting the first to-be-detected item and the second to-be-detected item. The modeling module may be specifically configured to: detect the first image and the second image based on the modeling models of the first to-be-detected item and the second to-be-detected item, to determine the detection results of the first to-be-detected item and the second to-be-detected item.

The apparatus may further include a determining module 914, which may be configured to determine whether the modeling models in the to-be-detected item modeling mode are invalid modeling models. The determining module may be specifically configured to: when time intervals between a first moment and moments at which the modeling models are established are greater than a threshold, determine that the modeling models are invalid modeling models, where the first moment is a moment at which the apparatus invokes the modeling model. The modeling module may be specifically configured to: when the models are invalid modeling models, photograph a first image and a first modeling image based on the first photographing parameter, where the first modeling image is used to establish a modeling model for the first to-be-detected image; and photograph a second image and a second modeling image based on the second photographing parameter, where the second modeling image is used to establish a modeling model for the second to-be-detected image.

The apparatus may further include a display module 915, configured to display the result corresponding to the first to-be-detected item and the detection result corresponding to the second to-be-detected item (or display a result obtained by synthesizing the result corresponding to the first to-be-detected item and the detection result corresponding to the second to-be-detected item), generate corresponding skin care suggestions based on the detection results, and so on.

In this solution, a plurality of photos (the first image and the second image) are acquired by using different photographing parameters (the first photographing parameter and the second photographing parameter), so that it can be ensured that blur degrees of depth of field positions and detail parts in to-be-detected images obtained in different photographing modes all meet detection precision, to ensure accuracy of subsequent detection results. It should be noted that, because different focal lengths (the first focal length and the second focal length) and different light intensities (the first light intensity and the second light intensity) are used, object blur degrees of different depth of field positions and object detail clarity degrees in the first image and the second image are different. The different focal lengths correspond to the object blur degrees of the different depths of field positions, and the different light intensities correspond to the different object detail clarity degrees. In addition, all photographing processes of the method are subject to fully automatic continuous photographing, so that a user does not need to manually adjust a focal length and a light intensity, thereby improving user experience. An embodiment of the present invention provides an image processing terminal, which may specifically include: the terminal shown in FIG. 2. The terminal includes: one or more processors 240, a memory 220, a plurality of application programs (stored in the memory 220), a light emitting diode LED (a flash may include the light emitting diode LED), and one or more computer programs. The one or more computer programs are stored in the memory, the one or more computer programs include an instruction, and when the instruction is executed by the terminal, the terminal is enabled to perform the following steps: acquiring at least one first image based on a first photographing parameter, where the first image includes a first to-be-detected item; and acquiring at least one second image based on a second photographing parameter, where the second image includes a second to-be-detected item, the first photographing parameter includes a first light intensity and a first focal length, and the second photographing parameter includes a second light intensity and a second focal length. The LED provides an LED light source, the LED light source emits light in a first mode to provide the first light intensity, and the LED light source emits light in a second mode to provide the second light intensity.

The first mode may include at least one of a flashlight mode, a preset light emitting mode, or a flash mode, an operating current of the LED light source in the flashlight mode is a first current, and an operating current of the LED light source in the preset light emitting mode is a second current. The second mode may include at least one of the flashlight mode, the preset light emitting mode, or the flash mode. Light intensities and lighting times in the flashlight mode and the preset light emitting mode are adjustable. A manner of adjusting the first focal length and the second focal length includes at least one of point focusing, area focusing, or full-face focusing. A manner of adjusting the first focal length and the second focal length includes at least one of point focusing, area focusing, or full-face focusing.

The first to-be-detected item and the second to-be-detected item may include at least one of the following: a skin tone, a speckle, redness, acne, oil content, a wrinkle, an eye feature, a blackhead, water content, melanin, porphyrin, or a pore. The eye feature includes at least one of under-eye puffiness, an under-eye dark circle, or an under-eye fine line. The wrinkle includes at least one of a nasolabial fold, a forehead wrinkle, a mountain root wrinkle, an upper lip wrinkle, or a downward wrinkle at a corner of a mouth. The water content includes at least one of water content of epidermis or water content of dermis.

Specifically, the first to-be-detected item may be classified into a first feature and a second feature based on a skin characteristic. The first feature includes at least one of the following: the skin tone, the speckle, or the redness. The second feature includes at least one of the following: the acne, the oil content, the wrinkle, the eye feature, the blackhead, the water content, the melanin, the porphyrin, or the pore. The second to-be-detected item may be classified into a third feature and a fourth feature based on a skin characteristic. The third feature includes at least one of the following: the blackhead, the eye feature, the melanin, the porphyrin, or the pore. The fourth feature includes at least one of the following: the skin tone, the speckle, the redness, the acne, the oil content, the wrinkle, or the water content. The eye feature includes at least one of the following: the under-eye puffiness, the under-eye dark circle, or the under-eye fine line. The wrinkle includes at least one of the following: the nasolabial fold, the forehead wrinkle, the mountain root wrinkle, the upper lip wrinkle, or the downward wrinkle at the corner of the mouth. The water content includes at least one of the following: the water content of epidermis or the water content of dermis.

The terminal may further perform the following step: detecting the first image and the second image, to determine detection results of the first to-be-detected item and the second to-be-detected item.

The terminal may specifically perform the following step: detecting the first image and the second image, to separately determine the detection results of the first to-be-detected item and the second to-be-detected item, where the first image includes the first to-be-detected item, and the second image includes the second detection item. In another optional implementation, the terminal may specifically perform the following steps: when there are a plurality of to-be-detected images, synthesizing the to-be-detected images into one detection image, and determining the detection results of the first to-be-detected item and the second to-be-detected item based on the synthesized to-be-detected image.

The terminal may specifically perform the following steps: when there are a plurality of to-be-detected images, detecting each of the plurality of to-be-detected images, to determine detection results corresponding to the first to-be-detected item and the second to-be-detected item in each to-be-detected image; and synthesizing detection results of all the images, to determine the detection results of the first to-be-detected item and the second to-be-detected item.

The terminal may specifically perform the following steps: when at least one of the first to-be-detected item in the first image or the second to-be-detected item in the second image is in a blurred state, deleting at least one of the first image or the second image; re-determining at least one of the first photographing parameter or the second photographing parameter, to acquire at least one of the first image or the second image; and determining a detection result of the at least one of the first to-be-detected item or the second to-be-detected item based on the at least one of the re-acquired first image or the re-acquired second image.

The terminal may further perform the following step: determining to enter a to-be-detected item modeling mode, where the to-be-detected item modeling mode includes modeling models for detecting the first to-be-detected item and the second to-be-detected item.

The terminal may specifically perform the following step: detecting the first image and the second image based on the modeling models of the first to-be-detected item and the second to-be-detected item, to determine the detection results of the first to-be-detected item and the second to-be-detected item.

The terminal may further perform the following step: determining whether the modeling models in the to-be-detected item modeling mode are invalid modeling models.

The terminal may specifically perform the following step: when time intervals between a first moment and moments at which the modeling models are established are greater than a threshold, determining that the modeling models are invalid modeling models, where the first moment is a moment at which the terminal invokes the modeling model.

The terminal may specifically perform the following steps: when the models are invalid modeling models, photographing a first image and a first modeling image based on the first photographing parameter, where the first modeling image is used to establish a modeling model for the first to-be-detected image; and photographing a second image and a second modeling image based on the second photographing parameter, where the second modeling image is used to establish a modeling model for the second to-be-detected image.

The terminal may specifically perform the following steps: when the terminal meets a photographing condition, acquiring at least one first image based on the first photographing parameter, and acquiring at least two second images based on the second photographing parameter, where the photographing condition includes an ambient light intensity and determining that the first to-be-detected item and the second to-be-detected item are within a photographing range.

It should be noted that a detection result corresponding to a final to-be-detected item and a suggestion made based on the detection result may be displayed by the display unit 230.

In this solution, a plurality of photos (the first image and the second image) are acquired by using different photographing parameters (the first photographing parameter and the second photographing parameter), so that it can be ensured that blur degrees of depth of field positions and detail parts in to-be-detected images obtained in different photographing modes all meet detection precision, to ensure accuracy of subsequent detection results. It should be noted that, because different focal lengths (the first focal length and the second focal length) and different light intensities (the first light intensity and the second light intensity) are used, object blur degrees of different depth of field positions and object detail clarity degrees in the first image and the second image are different. The different focal lengths correspond to the object blur degrees of the different depths of field positions, and the different light intensities correspond to the different object detail clarity degrees. In addition, all photographing processes of the method are subject to fully automatic continuous photographing, so that a user does not need to manually adjust a focal length and a light intensity, thereby improving user experience.

All or some of the foregoing embodiments may be implemented by using software, hardware, firmware, or any combination thereof. When software is used to implement the embodiments, the embodiments may be implemented completely or partially in the form of a computer program product. The computer program product includes one or more computer instructions. When the computer program instructions are loaded and executed on a computer, the procedure or functions according to the embodiments of the present invention are all or partially generated. The computer may be a general-purpose computer, a dedicated computer, a computer network, or other programmable apparatuses. The computer instructions may be stored in a computer readable storage medium or may be transmitted from a computer readable storage medium to another computer readable storage medium. For example, the computer instructions may be transmitted from a website, computer, server, or data center to another website, computer, server, or data center in a wired (for example, a coaxial cable, an optical fiber, or a digital subscriber line (DSL)) or wireless (for example, infrared, radio, or microwave) manner. The computer readable storage medium may be any usable medium accessible by a computer, or a data storage device, such as a server or a data center, integrating one or more usable media. The usable medium may be a magnetic medium (for example, a floppy disk, a hard disk, or a magnetic tape), an optical medium (for example, a DVD), a semiconductor medium (for example, a solid-state drive Solid State Disk (SSD)), or the like.

The objectives, technical solutions, and benefits of the present invention are further described in detail in the foregoing specific embodiments. It should be understood that the foregoing descriptions are merely specific embodiments of the present invention, but are not intended to limit the protection scope of the present invention. Any modification, equivalent replacement, or improvement made based on the technical solution of the present invention shall fall within the protection scope of the present invention.

What is claimed is:

1. An image acquisition method implemented by a terminal comprising a light-emitting diode (LED) light source, wherein the image acquisition method comprises:

acquiring, using a first photographing parameter, a first image comprising a first to-be-detected item, wherein the first photographing parameter comprises a first light intensity or a first focal length determined based on the first to-be-detected item;

acquiring, using a second photographing parameter, a second image comprising a second to-be-detected item, wherein the second photographing parameter comprises a second light intensity or a second focal length determined based on the second to-be-detected item, and wherein the second to-be-detected item and the second photographing parameter are different than the first to-be-detected item and the first photographing parameter;

emitting, using the LED light source, a first light in a first mode to provide the first light intensity, wherein the first mode includes at least one of a flashlight mode, a preset light emitting mode, or a flash mode, and wherein each of the flashing mode, the present light emitting mode, and the flash mode is configured with a different respective combination of intensity with emitting time than the other modes; and emitting, using the same LED light source, a second light in a second mode to provide the second light intensity, wherein the second mode includes at least one of the flashlight mode, the preset light emitting mode, or the flash mode, wherein the second mode is different than the first mode, and wherein the LED light source emits light with different respective combinations of intensity with emitting time in the first mode and the second mode.

2. The image acquisition method of claim 1, further comprising entering to a modeling mode comprising modeling models for detecting the first to-be-detected item and the second to-be-detected item.

3. The image acquisition method of claim 2, further comprising determining whether the modeling models are invalid modeling models.

4. The image acquisition method of claim 3, further comprising:
invoking the modeling models at a first moment; and
determining that the modeling models are the invalid modeling models when time intervals between the first moment and moments when the modeling models are established are greater than a threshold.

5. The image acquisition method of claim 3, wherein when the modeling models are the invalid modeling models, the image acquisition method further comprises:
photographing the first image and a first modeling image based on the first photographing parameter, wherein the first modeling image establishes a first modeling model for the first to-be-detected item; and
photographing the second image and a second modeling image based on the second photographing parameter, wherein the second modeling image establishes a second modeling model for the second to-be-detected item.

6. The image acquisition method of claim 1, wherein when the terminal meets a photographing condition, the image acquisition method further comprises:
further acquiring the first image based on the first photographing parameter; and
further acquiring the second image based on the second photographing parameter, wherein the photographing condition comprises an ambient light intensity, and wherein the first to-be-detected item and the second to-be-detected item are within a photographing range.

7. The image acquisition method of claim 1, wherein the first to-be-detected item and the second to-be-detected item include at least one of a skin tone, a speckle, redness, acne, oil content, a wrinkle, an eye feature, a blackhead, water content, melanin, porphyrin, or a pore.

8. The image acquisition method of claim 7, wherein the eye feature includes at least one of under-eye puffiness, an under-eye dark circle, or an under-eye fine line, wherein the wrinkle includes at least one of a nasolabial fold, a forehead wrinkle, a mountain root wrinkle, an upper lip wrinkle, or a downward wrinkle at a corner of a mouth, and wherein the water content includes at least one of water content of epidermis or water content of dermis.

9. An electronic device comprising:
a non-transitory memory configured to store instructions;
a processor coupled to the non-transitory memory, wherein the instructions cause the processor to be configured to:
acquire, using a first photographing parameter, a plurality of first images comprising a first to-be-detected item, wherein the first photographing parameter comprises a first light intensity and or first focal length determined based on the first to-be-detected item;
acquire, using a second photographing parameter, a plurality of second images comprising a second to-be-detected item, wherein the second photographing parameter comprises a second light intensity or a second focal length determined based on the second to-be-detected item, and wherein the second to-be-detected item and the second photographing parameter are different than the first to-be-detected item and the first photographing parameter;
detect the first to-be-detected item by performing first comprehensive processing in the plurality of first images, wherein the first comprehensive processing includes at least one of obtaining an average value, a maximum value, a minimum value, or a median value of the plurality of first images; and
detect the second to-be-detected item by performing second comprehensive processing in the plurality of second images, wherein the second comprehensive processing includes at least one of obtaining an average value, a maximum value, a minimum value, or a median value of the plurality of second images, and wherein the second comprehensive processing is different than the first comprehensive processing; and
a light-emitting diode (LED) light source coupled to the processor and configured to:
emit a first light in a first mode to provide the first light intensity, wherein the first mode includes at least one of a flashlight mode, a preset light emitting mode, or a flash mode, and wherein each of the flashing mode, the present light emitting mode, and the flash mode is configured with a different respective combination of intensity with emitting time than the other modes; and
emit a second light in a second mode to provide the second light intensity, wherein the second mode includes at least one of the flashlight mode, the preset light emitting mode, or the flash mode, wherein the second mode is different than the first mode, and wherein the LED light source emits light with different respective combinations of intensity with emitting time in the first mode and the second mode.

10. The electronic device of claim 9, wherein the instructions further cause the processor to be configured to enter to a modeling mode comprising modeling models for detecting the first to-be-detected item and the second to-be-detected item.

11. The electronic device of claim 10, wherein the instructions further cause the processor to be configured to determine whether the modeling models are invalid modeling models.

12. The electronic device of claim 11, wherein the instructions further cause the processor to be configured to:
invoke the modeling models at a first moment; and
determine that the modeling models are the invalid modeling models when time intervals between the first moment and moments when the modeling models are established are greater than a threshold.

13. The electronic device of claim 11, wherein when the modeling models are the invalid modeling models, the instructions further cause the processor to be configured to:

photograph the first image and a first modeling image based on the first photographing parameter, wherein the first modeling image establishes a first modeling model for the first to-be-detected item; and photograph the second image and a second modeling image based on the second photographing parameter, wherein the second modeling image establishes a second modeling model for the second to-be-detected item.

14. The electronic device of claim 9, wherein when the electronic device meets a photographing condition, the instructions further cause the processor to be configured to:

further acquire the first image based on the first photographing parameter; and further acquire the second image based on the second photographing parameter, wherein the photographing condition comprises an ambient light intensity, and wherein the first to-be-detected item and the second to-be-detected item are within a photographing range.

15. A computer program product comprising computer-executable instructions stored on a non-transitory computer readable medium that, when executed by a processor, cause a terminal to:

emit, using a light emitting diode (LED) light source, a first light in a first mode to provide a first light intensity, wherein the first mode includes at least one of a flashlight mode, a preset light emitting mode, or a flash mode, and wherein each of the flashing mode, the present light emitting mode, and the flash mode is configured with a different respective combination of intensity with emitting time than the other modes;

emit, using the same LED light source, a second light in a second mode to provide a second light intensity, wherein the second mode includes at least one of the flashlight mode, the preset light emitting mode, or the flash mode, wherein the second mode is different than the first mode, and wherein the LED light source emits light with different respective combinations of intensity with emitting time in the first mode and the second mode;

acquire, using a first photographing parameter, a first image comprising a first to-be-detected item, wherein the first photographing parameter comprises the first light intensity or a first focal length determined based on the first to-be-detected item; and acquire, using a second photographing parameter, a second image comprising a second to-be-detected item, wherein the second photographing parameter comprises the second light intensity or a second focal length determined based on the second to-be-detected item, and wherein the second to-be-detected item and the second photographing parameter are different than the first to-be-detected item and the first photographing parameter.

16. The computer program product of claim 15, wherein the computer-executable instructions further cause the terminal to enter to a modeling mode comprising modeling models for detecting the first to-be-detected item and the second to-be-detected item.

17. The computer program product of claim 16, wherein the computer-executable instructions further cause the terminal to determine whether the modeling models are invalid modeling models.

18. The computer program product of claim 17, wherein the computer-executable instructions further cause the terminal to:

invoke the modeling models at a first moment; and determine that the modeling models are the invalid modeling models when time intervals between the first moment and moments when the modeling models are established are greater than a threshold.

19. The computer program product of claim 17, wherein when the modeling models are the invalid modeling models, the computer-executable instructions further cause the terminal to:

photograph the first image and a first modeling image based on the first photographing parameter, wherein the first modeling image establishes a first modeling model for the first to-be-detected item; and photograph the second image and a second modeling image based on the second photographing parameter, wherein the second modeling image establishes a second modeling model for the second to-be-detected item.

20. The computer program product of claim 15, wherein when the terminal meets a photographing condition, the computer-executable instructions further cause the terminal to:

further acquire the first image based on the first photographing parameter; and further acquire the second image based on the second photographing parameter, wherein the photographing condition comprises an ambient light intensity, and wherein the first to-be-detected item and the second to-be-detected item are within a photographing range.

* * * * *